United States Patent [19]

Lunn

[11] Patent Number: 4,503,052
[45] Date of Patent: Mar. 5, 1985

[54] 7-(2-(SUBSTITUTED CINNOLINOYL)AMINO)ACETAMIDO)-1-OXA-BETA-LACTAMS

[75] Inventor: William H. W. Lunn, Indianapolis, Ind.

[73] Assignee: Eli Lilly and Company, Indianapolis, Ind.

[21] Appl. No.: 494,830

[22] Filed: May 16, 1983

[51] Int. Cl.$^3$ .................. A61K 31/535; C07D 498/04
[52] U.S. Cl. ...................................... 514/210; 544/90; 544/92
[58] Field of Search ................. 544/90, 92; 424/248.5, 424/248.51, 248.54

[56] References Cited

U.S. PATENT DOCUMENTS

| 3,669,965 | 6/1972 | White | 260/250 A |
|---|---|---|---|
| 4,125,611 | 11/1978 | Yamada et al. | 424/246 |
| 4,160,087 | 7/1979 | Yamada et al. | 544/28 |
| 4,198,504 | 4/1980 | Naito et al. | 544/25 |
| 4,226,866 | 10/1980 | Christensen et al. | 424/248.51 |
| 4,288,590 | 9/1981 | Oka et al. | 544/25 |
| 4,347,470 | 11/1982 | Watanabe et al. | 544/27 |
| 4,352,801 | 10/1982 | Nomoto et al. | 424/246 |
| 4,368,198 | 1/1983 | Yamada et al. | 424/246 |

FOREIGN PATENT DOCUMENTS 52-106885  9/1977  Japan .
52-106886  9/1977  Japan .
52-156893  12/1977  Japan .

OTHER PUBLICATIONS

Derwent Abstract 87992D of Japanese Unexamined Pat. No. J5 6131-592, (Bristol Banyo KK), Mar. 18, 1980.
Derwent Abstract 33812E of Japanese Unexamined Pat. No. J5 7046-990, (Fujimoto Seiyaku KK), Sep. 3, 1980.

Primary Examiner—Richard L. Raymond
Attorney, Agent, or Firm—Nancy J. Harrison; Arthur R. Whale

[57] ABSTRACT

1-Oxa-beta-lactam antibiotics of the formula are broad spectrum antibiotics especially useful in the treatment of infections attributable to the gram-negative microorganisms such as Pseudomonas or are intermediates to such antibiotics.

32 Claims, No Drawings

7-(2-(SUBSTITUTED CINNOLINOYL)AMINO)ACETAMIDO)-1-OXA-BETA-LACTAMS

SUMMARY OF THE INVENTION

1-Oxa-beta-lactam antibiotics of the formula

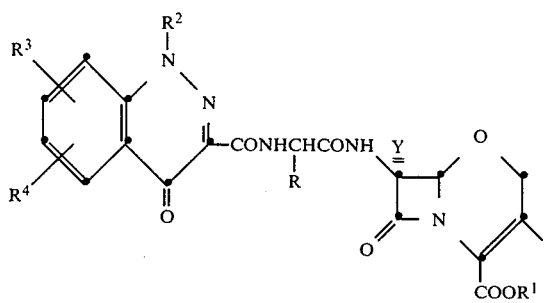

are broad spectrum antibiotics especially useful in the treatment of infections attributable to gram-negative microorganisums or are intermediates to such antibiotics. Methods of treating infections caused by gram-negative microorganisms, especially Pseudomonas species, and pharmaceutical compositions comprising the active compounds are also part of this invention.

DETAILED DESCRIPTION OF THE INVENTION

This invention is directed to new 1-oxa-beta-lactam compounds represented by the following general formula

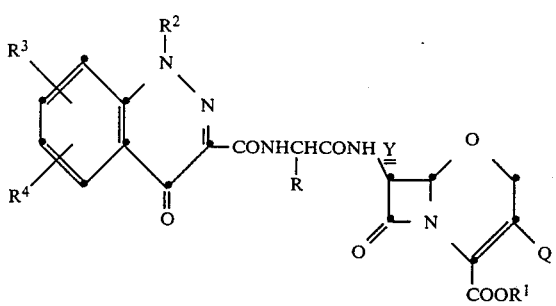

wherein:
R is phenyl which is optionally substituted by one or two hydroxy or $C_1$-$C_3$-alkoxy groups; cyclohexadienyl; cyclohexenyl; or 2-thienyl, 3-thienyl, 2-furyl, 3-furyl or 2-aminothiazol-4-yl, each of which is optionally substituted by one or two $C_1$-$C_3$-alkyl groups;

$R^1$ is hydrogen, a carboxy-protecting group or a biologically labile ester group;

$R^2$ is hydrogen, $C_1$-$C_3$-alkyl, acetyl, or $C_1$-$C_3$-alkylsulfonyl;

$R^3$ and $R^4$, independently, are hydrogen, hydroxy, $C_1$-$C_3$-alkoxy, $C_1$-$C_3$-alkyl, halo, $C_2$-$C_4$-alkanoyloxy, $C_1$-$C_3$-alkylsulfonyl, or $C_1$-$C_4$-alkylaminocarbonloxy; or $R^3$ and $R^4$, when taken together on adjacent carbon atoms, form an $$-O-CH_2-O- \text{ or } -O-\underset{\underset{N(CH_3)_2}{|}}{CH}-O- \text{ group;}$$

Y is hydrogen or methoxy;

Q is halo, methoxy, methyl or a group of the formula $-CH_2Q^1$ wherein $Q^1$ is
(a) $C_2$-$C_4$-alkanoyloxy;
(b) carbamoyloxy or $C_1$-$C_4$-alkylcarbamoyloxy;
(c) $C_1$-$C_4$-alkoxy;
(d) chloro, bromo or iodo;
(e) a heteroaryl group selected from

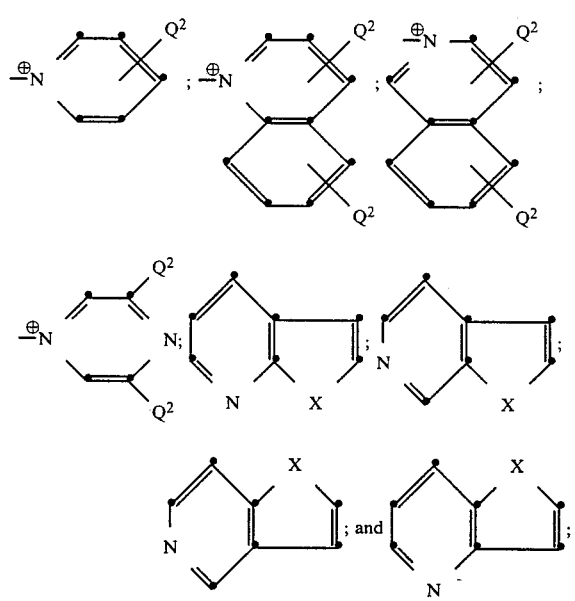

wherein
X is O, S, or —NH—;
$Q^2$ is hydrogen, $C_1$-$C_4$-alkyl,

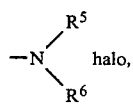

hydroxy, hydroxymethyl, trifluoromethyl, carbamoyl, $C_1$-$C_4$-alkylcarbamoyl, carboxy, cyano, $C_1$-$C_3$-alkanoyl,

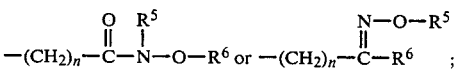

and $R^5$ and $R^6$, independently, are hydrogen of $C_1$-$C_4$-alkyl;
(f) a group of the formual —$SQ^3$
wherein $Q^3$ is
(a') $C_1$-$C_4$-alkyl, phenyl or phenyl substituted with 1 or 2 groups selected from the group consisting of $C_1$-$C_4$-alkyl, $C_1$-$C_4$-alkoxy, halo, hydroxy, nitro, cyano, methanesulfonamido and trifluoromethyl;
(b') a tetrazolyl group selected from

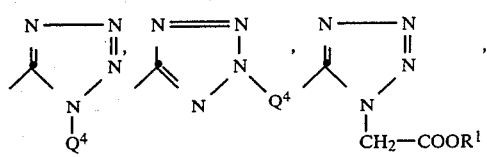
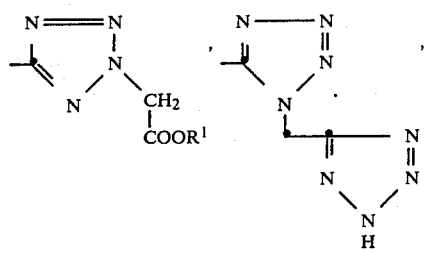
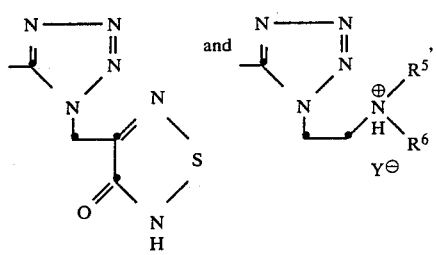
wherein Y is halo,
(c') a thiadiazolyl group selected from
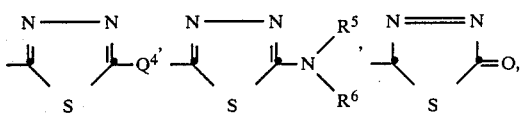
(d') an oxadiazolyl group of the formula
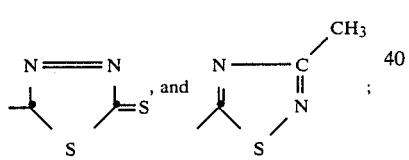
(e') a triazolyl group selected from
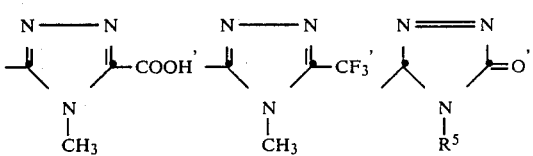
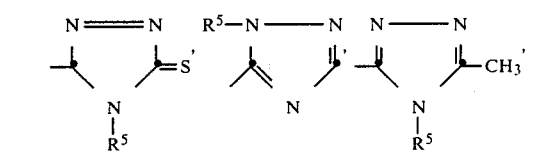
-continued
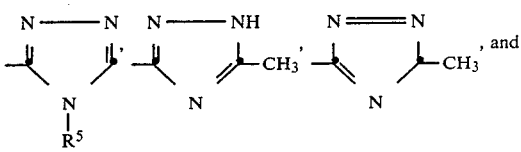
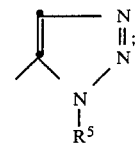
(f') a thiazolyl group selected from
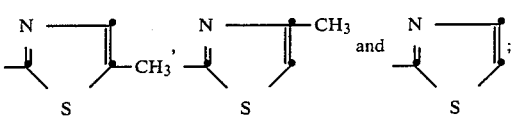
(g') an isothiazolyl group of the formula
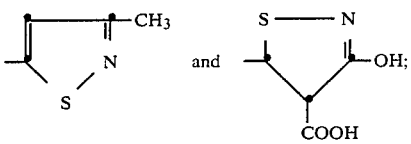
(h') an oxazolyl group of the formula
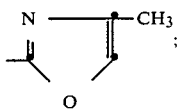
(i') a triazinyl group selected from
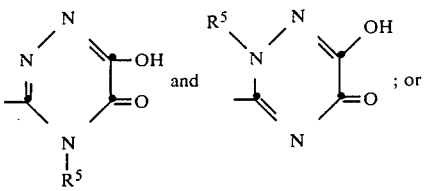
(j') a heteroaryl group selected from
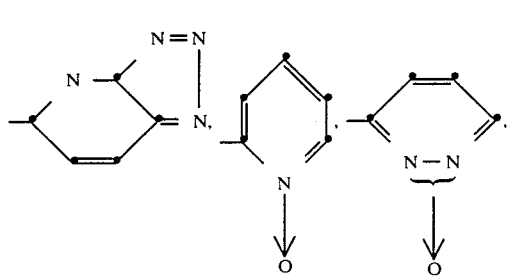

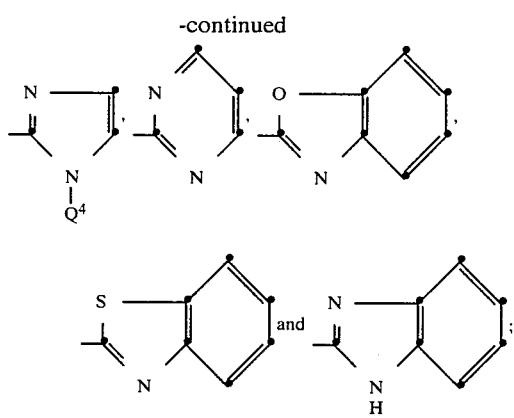

wherein $Q^4$ is hydrogen, $C_1$-$C_4$-alkyl, amino-$C_2$-14 $C_4$-alkyl, protected amino-$C_2$-$C_4$-alkyl or hydroxy-$C_2$-$C_4$-alkyl; and the salts, especially the phaarmaceutically acceptable salts, of the formula 1 acids.

In the definition of the compounds of this invention "halo" refers to fluoro, chloro or bromo, preferably fluoro or chloro.

In the terms "$C_1$—$C_{3(or\ 4)}$-alkyl", "$C_1$-$C_{3(or\ 4)}$-alkoxy", "$C_1$-$C_4$-alkanoyloxy" and "$C_2$-$C_4$-alkylaminocarbonyloxy", the alkyl portion of the group can be straight or branched. The term "$C_1$-$C_4$-alkanoyloxy" encompasses acetoxy, propanoyloxy, n-butyryloxy, isobutyryloxy and like groups. Representative "$C_1$-$C_4$-alkylaminocarbonyloxy" groups are methylcarbamoyloxy, ethylcarbamoyloxy, N,N-dimethylcarbamonyloxy, isopropylcarbamoyloxy and the like.

The alkoxy groups include methoxy, ethoxy, propoxy, isopropoxy, n-butoxy, isobutoxy, sec-butoxy and tert-butoxy. The alkyl groups include methyl, ethyl, propyl, isopropyl, n-butyl, isobutyl, tert-butyl, and sec-butyl.

The term "carboxy-protecting group" refers to those used in the field of penicillins and cephalosporins, especially ester-forming groups which can be removed under mild conditions hydrogenation or hydrolysis of other treatments. Such carboxy-protecting groups include, for example, benzyl; diphenylmethyl; p-nitrobenzyl; p-methyoxybenzyl; phenacyl; halogenated phenacyl; haloalkyl, for example, iodomethyl, 2,2,2-trichloroethyl, and 2,2,2-tribromoethyl; and branched alkyl, alkenyl, and alkynyl esters such as t-butyl, 3-methylbutene-1-3-yl, and isopentenyl.

The term "biologically labile ester group" refers to thsoe ester-forming groups which can easily be split off in the living organism. Such groups etc. for example, alkanoyloxyalkyl of the type

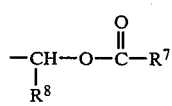

wherein $R^7$ is $C_1$-$C_4$-alkyl, phenyl or phenyl-$C_1$-$C_3$ alkyl and $R^8$ is hydrogen or $C_1$-$C_3$-alkyl. Acetoxymethyl, propionyloxymethyl, 2-acetoxyethyl and pivaloyloxymethyl are examples of alkanoyloxyalkyl groups. Other exemplary biologically labile ester groups are the phthalidyl and indanyl moieties.

Illustrative C-3 sustituents represented by the group —$CH_2SQ^3$ wherein $Q^3$ is $C_1$-$C_4$-alkyl, phenyl, or substituted pheny are methylthiomethyl, (n-propyl)-thiomethyl, phenylthiomethyl, (4-methylphenyl)thiomethyl, (4chlorophenyl)thiomethyl, (2-bromophenyl)thiomethyl, (3-nitrophenyl)thiomethyl, (2-methoxyphenyl)thiomethyl, (3-cyanophenyl)thiomethyl, (3,4-dichlorophenyl)thiomethyl, (4-methanesulfonamidophenyl)-thiomethyl, (4-trifluoromethylphenyl)thiomethyl, (3-chloro-4-hydroxyphenyl)thiomethyl and (3-methyl-4-chlorophenyl)thiomethyl.

When $Q^3$ is a tetrazolyl group, representative groups are 1-methyltetrazol-5-yl, 1-isopropyltetrazol-5-yl, 2-ethyltetrazol-5-yl, 1-(carboxymethyl)tetrazol-5yl, tetrazol-5-yl, 1-[(tert-butoxycarbonyl)aminomethyl]tetrazol-5-yl, 2-methyltetrazole-5-yl, 1-(hydroxyethyl)tetrazol-5-yl and 1-ethyltetrazol-5-yl.

When $Q^3$ is a thiadiazolyl group, representative groups are 2-methyl-1,3,4-thiadiazol-5-yl, 1,3,4-thiadiazol-5-yl, 2-(N,N-dimethylamino)-1,3,4-thiadiazol-5-yl, 2-oxo-1,3,4-(5H)thiadizol-5-yl, 2-thioxo-1,3,4-(5H)thiadiazol-5-yl, and 3-methyl-1,2,4-thiadiazol-5-yl.

When $Q^3$ is an oxadiazolyl group, illustrative groups are 1,3,4-oxadiazole-5-yl, 2-methyl-1,3,4-oxadiazol-5-yl and 2-ethyl-1,3,4-oxadiazol-5-yl.

When $Q^3$ is a triazolyl group, representative groups are 1-methyl-2-carboxyl-1,3,4-triazol-5-yl, 1-methyl-2-trifluoromethyl-1,3,4-triazol-5-yl, 1-methyl2-oxo-5H, 1,3,4-triazol-5-yl, 1-(n-propyl)-2-oxo-5H-1,3,4-triazol-5-yl, 1-methyl-2-thioxo-5H-1,3,4-triazol-5-yl, 4-methyl-1,3,4-triazol-5-yl, 1-ethyl-2-methyl-1,3,4-triazol-5-yl, 1,2-dimethyl-1,3,4-triazol-5-yl, 2-methyl-1H-1,3,4-triazol-5-yl, 1H-b 1,3,4-triazol-2-yl, 1methyl-1,3,4-triazol-5-yl, 1-butyl-1,3,4-triazol-5-yl, 2-methyl-3H-1,3,4-triazol-5-yl, 2-methyl-2H-1,3,4-triazol-5-yl, 1H-1,2,3-triazol-5-yl, 1-methyl-1,2,3-triazol-5-yl and 1-ethyl-1,2,3-triazol-5-yl.

Illustrative groups when R is a substituted phenyl group are 4-hydroxyphenyl, 3-hydroxyphenyl, 4-hydroxy-3-chlorophenyl, 4-methylphenyl, 3-butylphenyl, 4-methoxyphenyl, 2-bromo-3-methoxyphenyl, 4-benzyloxyphenyl, 3-methanesulfonamidophenyl, 4-methanesulfonamidophenyl, 3-nitrophenyl, 4-trifluoromethylphenyl, 3-cyanophenyl and like groups.

The dihydrocinnolin-4-one group is formula 1 represented by the partial formula:

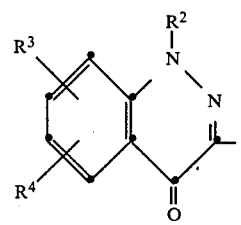

refers to groups such as 1,4-dihydro-1-ethyl-4-oxo-[1,3]dioxolo[4,5-g]cinnolinyl; 1,4-dihydro-6,7-dihydroxy-1-ethyl-4-oxo-cinnolin-3-yl; 6-acetyl-1,4-dihydro-4-oxo-cinnolin-3-yl; 1,4-dihydro-6,7-dihydroxy-1-methylsulfonyl-4-oxo-cinnolin-3-yl; 1,4-dihydro-1-ethyl-7-hydroxy-4-oxo-cinnolin-3-yl; 1,4dihydro-6,7-di(isopropoxy)-1-isopropylcinnolin-3-yl; 6-chloro-1,4-dihydro-1-methyl-4-oxo-cinnolin-3-yl; 1,4-dihydro-6,7-di(methylaminocarbonyloxy)-1-ethyl-4-oxo-cinnolin-3-yl; 1,4-dihydro-1-ethyl-6-(tert-butyl)-4-oxo-cinnolin-3-yl; 6,7-diacetoxy-1,4-dihydro-1-ethyl-4-oxo-cinnolin-3-yl; and the like.

When in the above formula, $R^1$ is hydrogen, the compounds of the invention can be converted to salts. Such salts are useful in the isolation and purification of the compounds and for administration of the compounds when used as antibiotics. Especially useful are the pharmaceutically acceptable salts such as, for example, (1) the alkali-metal and alkaline-earth-metal salts such as the sodium salt, the potassium salt, the lithium salt, and the calcium salts; (2) amine salts such as those formed with pharmaceutically acceptable amines such as procaine, abietyl amine, the ethanolamines, such as monoethanolamine and diethanolamine; and (3) the ammonium salt. The pharmaceutically acceptable salts can be formulated into useful parenteral dosage forms for administration of the antibiotics.

It will be recognized by those in the art that certain of the compounds of formula 1 can exist as tautomers, i.e. compounds having formula 2:

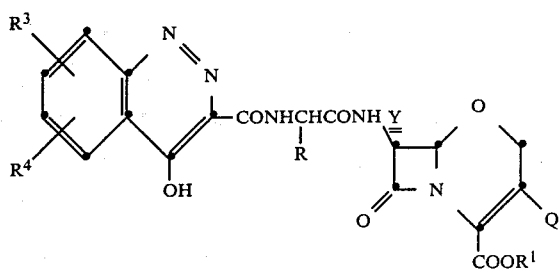

wherein R, $R^1$, $R^3$, $R^4$, Q and Y are as previously defined. The tautomeric forms, i.e. the compounds of formula 2, are also part of this invention and are prepared by similar methods.

The formula 1 and 2 compounds also have a chiral center at the carbon atoms to which the R-group is attached and may be present, therefore in two possible R- and S-configurations or as mixtures of these. If the end product is obtained in the D,L-form, the pure D- and L-diastereoisomers can be separated by preparative high pressure liquid chromatography (HPLC).

The 1-oxa-β-lactam compounds of formula 1 can be prepared by the following methods.

Method A:

By reacting a compound of formula 3

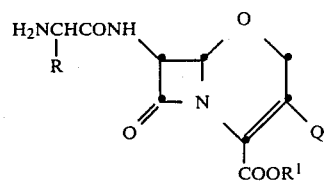

wherein Q, R and $R^1$ are as previously defined, with an activated derivative of a compound of formula 4:

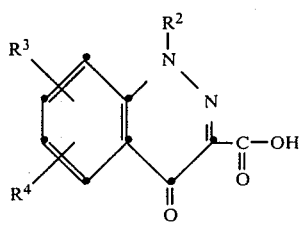

($R^2$, $R^3$ and $R^4$ have the meanings described supra.)

By the term "activated derivative" is meant a derivative which renders the carboxyl function of the formula 4 acylating agent reactive to coupling with the primary amino group of the formula 3 compound to form the amide bond. Suitable activated derivatives, their methods of preparation, and their methods of use as acylating agents for a primary amine will be recognized by those skilled in the art. Preferred activated derivatives are: (a) an acid halide (e.g. acid chloride), (b) an acid anhydride (e.g. an alkoxyformic acid anhydride or aryloxyformic acid anhydride) or (c) an activated ester (e.g. a 2,4,5-trichlorophenyl ester, an N-hydroxybenztriazole ester, or an N-hydroxysuccinimide ester). Other methods for activating the carboxyl function include reaction of the carboxylic acid with a coupling reagent such as carbonyldiimide (e.g. N,N-dicyclohexylcarbodiimide or N,N'-diisopropylcarbodiimide), carbonyldiimidazole or N-ethoxycarbonyl-2-ethoxy-1,2-dihydroquinoline. This gives a reactive intermediate which, because of instability, is not isolated, the reaction with the primary amine being carried out in situ. Of particular value when $R^3$ and $R^4$ are both hydroxy on adjacent carbon atoms is the Vilsmeier reagent,

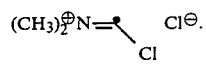

This reagent can be prepared from dimethylformamide and, for example, thionyl chloride. Use of the Vilsmeier reagent allows for protection of the hydroxyl groups while at the same time forming the acid chloride, giving an acylating agent of formula 5

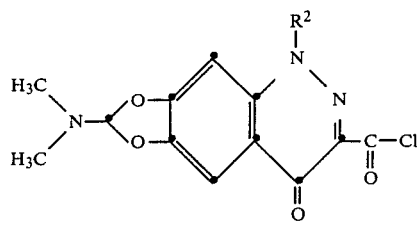

When $R^1$ is hydrogen, the starting compounds of formula 3 can be used in the form of their inorganic or organic salts, for instance as the triethylammonium salts or the sodium salts. In that case the reaction can be carried out in any desired mixtures of water and organic solvents which are miscible with water, such as ketones, for example, acetone; cyclic ethers, for example, tetrahydrofuran or dioxane; nitriles, for example acetonitrile; formamides, for example dimethylformamide; dimethyl sulfoxide; or alcohols, for example isopropanol; or in hexametalpol. By addition of a base or by use of a buffer solution, the pH of the reaction mixture is kept in a pH range of about 2.0 to 9.0, preferably between pH 6.5 and 8.0. However, it is also possible to carry out the reaction in an anhydrous organic solvent, such as halogenated hydrocarbons like chloroform or methylene chloride, in the presence of a base, preferably triethylamine, diethylamine or N-ethylpiperidine.

The reaction can further be carried out in a mixture of water and a water-immiscible solvent, such as an ether, for example diethyl ether; a halogenated hydrocarbon, for example chloroform or methylene chloride; carbon disulfide; a ketone; a ketone, for example isobutyl methyl ketone; an ester, for example ethyl acetate; or an aromatic solvent, for example benzene, where it is advantageous to stir vigorously and to keep the pH value in a range of about pH 2.0 to 9.0, preferably between 6.5 and 8.0, by addition of a base or by use of a buffer solution. The reaction can be carried out, however, also in water alone in the presence of an organic or inorganic base or a buffer substance.

When $R^1$ is trimethylsilyl, that is, if a silyl derivative of a compound of the formula 3, such as a mono- or, more advantageously, a di-trimethylsilyl derivative silylated at the amino and carboxyl group, is used as the starting compound, and it is reacted with a compound of the formula 4, the reaction is generally advantageously carried out in an anhydrous solvent or a solvent free from hydroxyl groups, for example in a halogenated hydrocarbon, such as methylene chloride or chloroform, benzene, acetonitrile, tetrahydrofuran, acetone or dimethylformamide, etc. The addition of a base is not usual, but may be of advantage in individual cases to improve the yield or the purity of the end product. Examples of such bases are tertiary aliphatic or aromatic amines, such as pyridine or triethylamine, or secondary amines which are difficult to acylate because of steric hindrance, such as dicyclohexylamine.

When $R^1$ is a carboxy-protecting group or a biologically labile ester group, such as diphenylmethyl or pivaloyloxymethyl, it is advantageous to perform the reaction in an aprotic solvent, such as absolute methylene chloride, chloroform, acetonitrile, tetrahydrofuran or dimethylformamide.

The amount of base to be used is determined, for example, by the desired maintenance of a certain pH value.

In general, all organic and inorganic bases which are usually used in organic chemistry, can be used as base additives. Such bases may be alkali metal and alkaline earth metal hydroxides, alkaline earth metal oxides, alkali metal and alkaline earth metal carbonates and bicarbonates, ammonia, primary, secondary and tertiary aliphatic and aromatic amines, as well as heterocyclic bases. Preferred bases are sodium, potassium and calcium hydroxide, calcium oxide, sodium and potassium carbonate, sodium and potassium bicarbonate, ethylamine, methylethylamine, triethylamine, hydroxyethylamine, aniline, dimethylaniline, pyridine and piperidine.

Suitable buffer systems include all the usual buffer mixtures, such as phosphate buffer, citrate buffer and tris(hydroxymethyl)-amino-methane buffer.

The reaction temperatures can be varied over a wide range. In general, the reaction is carried out between −20° and +50° C., preferably between 0° and +20° C.

The reactants of the formulas 3 and 4 can be reacted with each other in equimolar quantities. In some cases, however, it may be advantageous to use one of the reaction partners in excess to facilitate the purification of the end product or to increase the yield.

Method B:

By reacting a carboxylic acid of formula 6

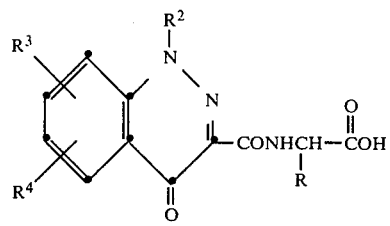

wherein R, $R^2$, $R^3$ and $R^4$ are as previously defined, or a salt of a reactive derivative thereof, with a 7-amino-1-oxa-$\beta$-lactam derivative of the formula

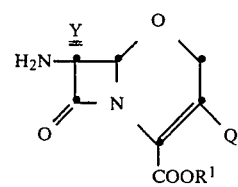

wherein $R^1$, Y and Q are as previously defined.

Essentially the same general reaction conditions described supra are applicable to the analogous steps, for example, silyl ester formation, activated derivative formation and acylation with the activated derivative.

In general, however, all methods of N-acylation which are known in $\beta$-lactam chemistry can be used.

The formula 7 compound is advantageously reacted in the form of an in vitro or in vivo easily cleavable derivative. For example, the formula 7 compounds wherein $R^1$ has the above-mentioned meanings, with the exception of hydrogen, are suitable. Especially preferred derivatives are the diphenylmethyl ester, tert-butyl ester, p-nitrobenzyl ester, trimethylsilyl ester or N,O-bis(trimethylsilyl) derivative.

For example, the carboxylic acid or a salt or reactive derivative thereof is reacted with the formula 7 compound in a solvent at temperatures between −20° and +40° C., optionally in the presence of a base. If, for example, an anhydride of the carboxylic acid, such as the anhydride with ethylchloroformate, is used, the reaction is carried out while cooling, for instance at −10° C. to +10° C., in the presence of a tertiary amine such as triethylamine or N,N-dimethylaniline, in a solvent such as acetone, tetrahydrofuran, dimethylformamide, chloroform, dichloromethane, hexametapol, or a mixture of these solvents. If, for example, an N-hydroxysuccinimide ester of the carboxylic acid is reacted with a formula 7 compound, the reaction is preferably carried out at 0° to 20° C. in the presence of a base such as triethylamine, in a solvent such as dimethylformamide, dichloromethane, dioxane, or a mixture of such solvents.

The reaction of carboxylic acid of the formula 6 or a salt thereof with a compound of the formula 7 is advantageously carried out in the presence of a condensation agent, for instance in the presence of N,N'-dicyclohexylcarbodiimide.

Method C:

By reacting a compound of formula 8

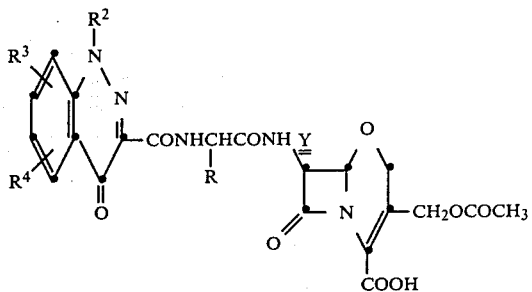

wherein R, $R^2$, $R^3$, $R^4$ and Y are as previously defined with a compound of formula 9

$$Q^3-S-M \qquad 9$$

wherein $Q^3$ is as previously defined, and M is hydrogen, an alkali metal or an alkaline-earth metal.

For example, a compound of the formula 8 is reacted with 5-methyl-2-mercapto-1,2,3,4-tetrazole in a solvent such as water, methanol, ethanol, acetone, methyl ethyl ketone, tetrahydrofuran, acetonitrile, ethyl acetate, dimethoxyethane, dimethylformamide, dimethyl sulfoxide, chloroform or a mixture of these solvents. Preferably, a strong polar solvent such as water or the like is used. In this case the pH of the reaction solution is advantageously maintained between 2 and 10, and particularly between 4 and 8. The desired pH value can be adjusted by addition of a buffer solution, such as sodium phosphate. Normally, the reaction is carried out at a temperature in a range of 0° to 100° C., over a reaction time of from about 1-2 hours.

Method D:

Method B is a preferred method for preparing a compound of the formula 1 wherein Y is methoxy. Such compounds can also be obtained, however, by reacting a compound of the formula 1 wherein Y is hydrogen, in the presence of methanol with an alkali metal methylate of the formula $M+OCH_3-$, where $M+$ is an alkali metal, and then with a halogenating agent. For this purpose, the formula 1 compound wherein Y is hydrogen is dissolved or suspended in an insert solvent, such as tetrahydrofuran, dioxane, ethylene glycol ether, methylene chloride, chloroform, dimethylformamide, methanol or the like or in a mixture of two of these solvents.

An alkali metal methylate together with methanol is added to the solution or suspension. After this reaction is complete, the mixture is then reacted with a halogenating agent. In this reaction methanol is used in excess, and the quantity of the alkali metal methylate is preferably 2 to 6 equivalents per equivalent of formula 1 starting compound. "Excess" means an amount of more than one equivalent per equivalent of the formula 1 starting material. All reactions are carried out at temperatures between $-120°$ C. and $-10°$ C., and preferably between $-100°$ and $-50°$ C. A reaction time of 5 to 30 minutes is sufficient. The reaction is terminated by acidifying the reaction system.

The halogenating agent used in this process is generally known as a source for positive halogen atoms, such as $Cl^+$, $Br^+$ or $I^+$. Examples of such halogenating agents are halogens, such as chlorine, bromine, etc.; N-halo-imides, such as N-chloro-succinimide, N-bromo-succinimide, and the like; N-halo-amides, such as N-chloroacetamide, N-bromoacetamide, etc.; N-halo-sulfonamides, such as N-chloro-benzenesulfonamide, N-chloro-p-toluenesulfonamide, etc.; 1-halo-benzotriazoles; 1-halo-triazines; organic hypohalites, such as tert. butylhypochlorite, tert. butylhypoiodite, etc.; and halo-hydantoins, such as N,N-dibromohydantoin, etc. Tert. butylhypochlorite is preferred among these halogenating agents. The halogenating agent is used in a quantity sufficient to release an equivalent quantity of positive halogen atoms with regard to the amount of formula 1 starting material used.

Suitable acids for termination of the reaction are those which do not lead to solidification of the reaction mixture or to freezing of the reaction mixture into a heavy viscous mass when they are added to the cold reaction mixture. Suitable acids are, for example, 98% formic acid, glacial acetic acid, trichloroacetic acid or methane sulfonic acid.

After termination of the reaction the excess halogenating agent is removed by treatment with a reducing agent, such as trialkyl phosphite, sodium thiosulfate or the like.

The compounds prepared according to methods A, B and D wherein $R^1$ is a carboxy-protecting group can be converted according to known methods in cephalosporin chemistry into the free carboxylic acids of the formula 1 wherein $R^1$ is hydrogen. Thus, the trimethylsilyl group can, for example, be easily removed by aqueous hydrolysis, and the benzhydryl group can be removed, for example, by hydrolytic cleavage with trifluoroacetic acid. This elimination of the protective groups is known in the art.

The formula 1 compounds wherein $R^1$ is hydrogen can be converted into the biologically labile acyloxyalkyl esters wherein $R^1$ is, for example, a pivaloyloxymethyl radical

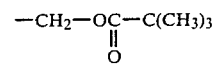

by reacting an alkali-metal salt of the corresponding carboxylic acid, for example, a sodium or potassium salt, with a pivaloyloxymethyl halide of the formula

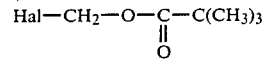

wherein Hal is chlorine, bromine or iodine. Further suitable acyloxyalkyl halides are, for example, chloromethyl acetate, bromomethyl propionate and 1-bromoethyl acetate.

The preparation of an acyloxyalkyl ester of formula 1 is carried out by reacting the respective alkali-metal salt of the parent acid in an inert solvent with a slight molar excess of the iodo-, bromo-or chloroalkyl ester, such as pivaloyloxymethyl iodide, at room temperature or slightly elevated temperature up to about 40° to 45° C. Suitable solvents are, for example, acetone, tetrahydrofuran, dioxane, dimethyl-formamide or methylene chloride An indanyl ester of the formula 1, wherein $R^1$ is

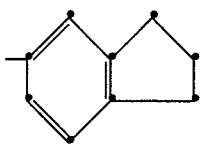

can be prepared by reacting 5-indanol in an inert solvent, such as dioxane or tetrahydrofuran, with the free acid form of a compound or formula 1 ($R^1$ is hydrogen) in the presence of a condensation agent, for example, a diimide such as N,N'-dicyclohexylcarbodiimide. The reaction is carried out while stirring at a temperature of about 20° to 35° C. during a reaction time of about 6 to 8 hours. For the isolation of the indanyl ester, the reaction mixture is first diluted with water, the insoluble dicyclohexylurea is filtered, and the ester is extracted from the filtrate.

The indanyl esters can also be prepared by reacting an anhydride, formed from a formula 1 acid and acetic acid, with 5-indanol.

A phthalidyl ester of formula 1, wherein $R^1$ is

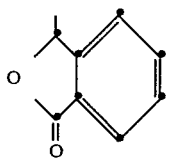

can be prepared by reacting the bromophthalide of the formula

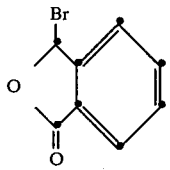

with a salt of a formula 1 acid. Esterification can be effected by slowly heating a mixture of equimolar amounts of the salt, e.g., a sodium or potassium salt, and bromophthalide in dimethylformamide, dimethyl-acetamide, dioxane, tetrahydrofuran or mixtures thereof.

The reaction mixtures obtained according to methods A-D are further processed by conventional methods for β-lactam antibiotics, including the isolation and purification of the end products, for instance concerning the liberation of the acid to form other salts with inorganic or organic bases. Especially suitable for the preparation of potassium or sodium salts is the precipitation of these salts from an alcoholic-ethereal solution of a free acid by addition of potassium or sodium 2-ethyl hexanoate, or the reaction of a free acid with the corresponding quantity of sodium bicarbonate under pH control and subsequent freeze-drying.

The starting materials of formulas 3 and 7 are known in the art. The α-amino-α-(substituted)-acetamideo side chain, common to the starting materials of formula 3, is typically disclosed as a side chain substituent in patents and other publications in the cephalosporin art. Thus, for example, starting materials of the formula 3 wherein R is phenyl, substituted phenyl or thienyl and wherein Q is a [1-substituted-tetrazol-5-yl]thiomethyl group or a [5-methyl-1,3,4-thiadiazol-2-yl]thiomethyl group are described in U.S. Pat. 4,138,486. The following table shows some sources of starting materials available for the preparation of the 7-[α-[(hydroxy-substituted aroyl)amino]-acetamido]-1-oxa-beta-lactam compounds of the present invention.

| Q | Source |
|---|---|
| —CH₃ | U.S. Pat. No. 4,143,038 |
| | U.S. Pat. No. 4,226,866 |
| —CH₂S—(N-N=N-N(CH₃)-N) and | U.S. Pat. No. 4,226,864 |
| | U.S. Pat. No. 4,138,486 |
| other —CH₂S—Het groups | | other -CH₂S-Het groups

Examples of starting materials which can be acylated to provide the novel compounds of the present invention are:

7-[D-[2-phenyl-2-aminoacetyl]amino]-3-methoxy-1-oxa-dethiaceph-3-em-4-carboxylic acid, 7-[D-[2-(4-hydroxyphenyl)-2-aminoacetyl]amino]-3-chloro-1-oxa-dethiaceph-3-em-4-carboxylic acid, 7-[D-[2-(3-chloro-4-hydroxyphenyl)-2-aminoacetyl]amino]-3-pyridiniummethyl-1-oxa-dethiaceph-3-em-4-carboxylic acid, 7-[D-[2-(2-thienyl)-2-aminoacetyl]amino]-3-[[1-methyltetrazol-5-yl)thio]methyl]-1-oxa-dethiaceph-3-em-4-carboxylic acid, 7-[D-[2-(1,4-cyclohexadienyl)-2-aminoacetyl]amino]-3-methyl-1-oxa-dethiaceph-3-em-4-carboxylic acid, 7-[D-[2-phenyl-2-aminoacetyl]amino]-3-carbamoyloxymethyl-1-oxa-dethiaceph-3-em-4-carboxylic acid, 7-[D-[2-(2-furyl)-2-aminoacetyl]amino]-3-[(4-carboxamidopyridinium)methyl]-1-oxa-dethiaceph-3-em-4-carboxylic acid, 7-[D-[2-(4-hydroxyphenyl)-2-aminoacetyl]amino]-3-phenylthiomethyl-1-oxa-dethiaceph-3-em-4-carboxylic acid, 7-[D-[2-(4-methylphenyl)-2-aminoacetyl]]amino]-3-bromo-1-oxa-dethiaceph-3-em-4-carboxylic acid, 7-[D-[2-phenyl-2-aminoacetyl]amino]-3-[[(2-oxo-1,3,4-(5H)thiadiazol-5-yl)thio]methyl]-1-oxa-dethiaceph-3-em-4-carboxylic acid, 7-[D-[2-(4-hydroxymethyl)-2-aminoacetyl]amino]-3-methylthiomethyl-1-oxa-dethiaceph-3-em-4-carboxylic acid, 7-[D-[2-(2-methoxyphenyl)-2-aminoacetyl]amino]-3[[(tetrazol-5-yl)thio]methyl]-1-oxa-dethiaceph-3-em-4-carboxylic acid, 7-[D-[2-(3-nitrophenyl)-2-aminoacetyl]amino]-3-[[(1-hydroxymethyltetrazol-5-yl)thio]methyl]-1-oxa-dethiaceph-3-em-4-carboxylic acid, 7-[D-[2-(3-methanesulfonamidophenyl)-2-aminoacetyl]amino]-3-[[(3-methyl-1,2,4-thiadiazol-5-yl)-thio]methyl]-1-oxa-dethiaceph-3-em-4-carboxylic acid, 7-[D-[2-(4-hydroxyphenyl)-2-aminoacetyl]amino]-3-[[(1-methyltetrazol-5-yl)thio]methyl]-1-oxa-dethiaceph-3-em-4carboxylic acid, 7-[D-(2-phenyl-2-aminoacetyl)amino]-3-[[(4-methyl-1,3,4-triazol-5-yl)thio]methyl]-1-oxa-dethiaceph-3-em-4-carboxylic acid, 7-[D-[2 -(2-thienyl)-2-aminoacetyl]amino]-3-[[(1-methyl-1,2,3-triazol-5-yl)thio]methyl]-1-oxa-dethiaceph-3-em-4-carboxylate, 7-[D-2-(3-thienyl)-2-aminoacetyl]amino]-3-acetoxymethyl-1-oxa-dethiaceph-3-em-4-carboxylic acid, 7-[D-(2-phenyl-2-aminoacetyl)amino]-3-methoxymethyl-1-oxa-dethiaceph-3-em-4-carboxylic acid, 7-[D-[2-(4hydroxyphenyl)-2-aminoacetyl]amino]-3-chloromethyl-1-oxa-dethiaceph-3-em-4carboxylic acid, 7-[D-2-(4-hydroxyphenyl)-2-aminoacetyl]amino]-3-[[(4,5-dihydro-6-hydroxy-4-methyl-5-oxo-1,2,4-triazin-3-yl)thio]methyl-1-oxa-dethiaceph-3-em-4-carboxylic acid, 7-[D-(2-phenyl-2-aminoacetyl)amino]-3-[[(4-methyloxazol-2-yl)thio]methyl]-1-oxa-dethiaceph-3-em-4-carboxylic acid, and 7-[D-(2-phenyl-2-aminoacetyl)amino]-3-[[(5-methyl-thiazol-2-yl)thio]methyl]-1-oxa-dethiaceph-3-em-4-carboxylic acid.

The L-isomers of these starting compounds can be used when the product L-isomer is desired. Alternatively, the D,L-mixture can be prepared and then separated to give the individual isomers.

Several of the starting materials of formula 4 are known in the art. For example, the formula 4 compounds wherein $R^3$ and $R^4$ together form an —O—CH$_2$—O— group are disclosed by W. A. White in U.S. Pat. No. 3,669,965.

The carboxylic acids of the formula 6 can be obtained by reacting a cinnoline compound of the formula 4 with a glycine derivative of formula

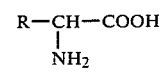

wherein R has the meanings previously defined. The reaction is carried out at temperatures between $-20°$ C. and $+40°$ C., preferably between $0°$ C. and $+20°$ C., in a solvent. Suitable solvents are, for example, mixtures of water and organic solvents which are miscible with water, such as acetone, tetrahydrofuran, dioxane, acetonitrile, dimethylformamide, ethanol or dimethyl sulfoxide, optionally in the presence of a hydrogenhalide binding agent. Suitable representatives thereof are, for example, trialkylamines such as triethylamine, or inorganic bases such as dilute sodium hydroxide.

Illustrative 1-oxa-β-lactam antibiotics of formula 1

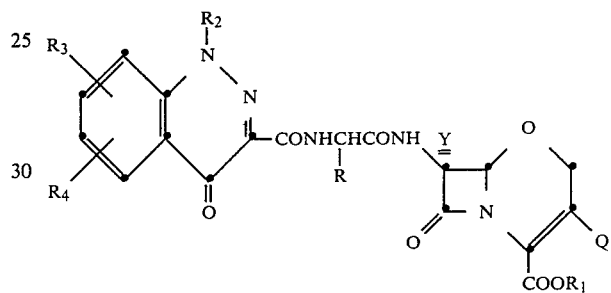

are the following compounds where $R^1$ is hydrogen:

| R | $R^2$ | $R^3$ | $R^4$ | Q |
|---|---|---|---|---|
| phenyl | ethyl | hydroxy | hydroxy | —CH$_2$S—⟨triazole ring with N, N, N, N–CH$_3$⟩ |
| 4-hydroxyphenyl | " | " | " | " |
| 3-chloro-4-hydroxyphenyl | " | " | " | " |
| 1,4-cyclohexadienyl | " | " | " | " |
| 2-thienyl | " | " | " | " |
| 2-furyl | " | " | " | " |
| 3-methansulfonamidophenyl | " | " | " | " |
| 3,4-dihydroxyphenyl | " | " | " | " |
| phenyl | H | " | " | " |
| 4-hydroxyphenyl | H | " | " | " |
| 1,4-cyclohexadienyl | H | " | " | " |
| 2-thienyl | H | " | " | " |
| phenyl | methyl | " | " | " |
| 4-hydroxyphenyl | " | " | " | " |
| 3-thienyl | " | " | " | " |
| 2-chlorophenyl | " | " | " | " |
| 1,4-cyclohexadienyl | " | " | " | " |
| 3-furyl | ethyl | " | " | " |
| 4-benzyloxyphenyl | " | " | " | " |
| 2-methoxyphenyl | " | " | " | " |
| 3-nitrophenyl | " | " | " | " |
| phenyl | " | acetyl | acetyl | " |
| 4-hydroxyphenyl | " | " | " | " |
| 3-bromo-4-hydroxyphenyl | " | " | " | " |
| 2-thienyl | " | " | " | " |
| phenyl | " | Cl | Cl | " |
| phenyl | " | hydroxy | H | " |
| phenyl | " | H | hydroxy | " |

-continued

| R | R² | R³ | R⁴ | Q |
|---|---|---|---|---|
| phenyl | " | acetoxy | H | " |
| 4-hydroxyphenyl | " | ethyl | ethyl | " |
| 4-hydroxyphenyl | " | hydroxy | " | " |
| 4-hydroxyphenyl | " | Cl | Cl | " |
| phenyl | " | hydroxy | hydroxy | $-CH_2S-\underset{S}{\underset{\|}{\overset{N-N}{\|}}}-CH_3$ |
| phenyl | H | " | " | " |
| phenyl | acetyl | " | " | " |
| 4-chlorophenyl | ethyl | " | " | " |
| 4-hydroxyphenyl | " | " | " | " |
| 3,4-dihydroxyphenyl | " | " | " | " |
| 2-thienyl | " | " | " | " |
| 1,4-cyclohexadienyl | " | " | " | " |
| phenyl | " | acetoxy | acetoxy | " |
| 3-chloro-4-methoxyphenyl | " | " | " | " |
| phenyl | methylsulfonyl | hydroxy | hydroxy | " |
| 4-hydroxyphenyl | " | " | " | " |
| " | ethyl | " | hydroxy | $-CH_2S-\underset{COOH}{\underset{\|}{\overset{S-N}{\|}}}-OH$ |
| phenyl | " | " | " | " |
| phenyl | " | " | " | $-CH_2S-\underset{S}{\underset{\|}{\overset{N=N}{\|}}}\!\!\!=\!\!O$ |
| 2-thienyl | " | " | " | " |
| phenyl | " | " | " | $-CH_2S-\underset{O}{\underset{\|}{\overset{N-N}{\|}}}-CH_3$ |
| phenyl | H | " | " | " |
| phenyl | ethyl | " | " | acetoxymethyl |
| phenyl | methyl | " | " | " |
| 4-hydroxyphenyl | ethyl | " | " | " |
| 2-thienyl | " | " | " | " |
| phenyl | " | methoxy | methoxy | " |
| phenyl | methyl | " | " | " |
| phenyl | " | acetoxy | acetoxy | " |
| 4-hydroxyphenyl | ethyl | hydroxy | hydroxy | methyl |
| phenyl | " | " | " | " |
| phenyl | H | H | H | " |
| phenyl | methyl | H | H | " |
| phenyl | ethyl | hydroxy | hydroxy | $-CH_2S-\underset{\underset{CH_3}{N}}{\underset{\|}{\overset{N-N}{\|}}}$ |
| 4-hydroxyphenyl | " | " | " | " |
| 1,4-cyclohexadienyl | " | " | " | " |
| 4-hydroxyphenyl | methyl | " | " | $-CH_2S-\underset{\underset{CH_3}{N}}{\underset{\|}{\overset{N-N}{\|}}}-CH_3$ |
| 4-hydroxyphenyl | ethyl | " | H | " |

-continued

| R | $R^2$ | $R^3$ | $R^4$ | Q |
|---|---|---|---|---|
| phenyl | " | " | hydroxy | " |
| phenyl | " | " | " | —CH₂S—[1-methyl-5-oxo-4,5-dihydro-1,2,4-triazol-3-yl] |
| 4-hydroxyphenyl | methyl | methyl | methyl | " |
| 2-furyl | " | hydroxy | H | " |
| 2-thienyl | ethyl | " | hydroxy | " |
| 4-methoxyphenyl | " | " | " | —CH₂S—[1-methyl-5-thioxo-4,5-dihydro-1,2,4-triazol-3-yl] |
| 4-trifluoromethylphenyl | " | " | " | " |
| 4-hydroxyphenyl | " | " | " | " |
| 2-thienyl | " | " | " | —CH₂S—[1H-1,2,3-triazol-4-yl] |
| phenyl | " | " | " | " |
| 4-hydroxyphenyl | " | " | " | " |
| 4-hydroxyphenyl | acetyl | " | " | " |
| 4-hydroxyphenyl | methylsulfonyl | " | " | " |
| phenyl | ethyl | " | " | —CH₂S—[4-methyl-oxazol-2-yl derivative] |
| 1,4-cyclohexadienyl | " | " | " | " |
| 4-hydroxyphenyl | " | " | " | —CH₂S—[thiazol-2-yl] |
| phenyl | " | " | " | —CH₂S—[pyridine N-oxide] |
| 2-thienyl | n-propyl | H | H | " |
| 4-hydroxyphenyl | ethyl | " | " | " |
| 3-methoxyphenyl | " | Cl | Cl | " |
| phenyl | " | hydroxy | hydroxy | —CH₂S—[1-methyl-5-hydroxy-6-oxo-1,6-dihydro-1,2,4-triazin-3-yl] |
| phenyl | acetyl | " | " | " |

-continued

| R | R² | R³ | R⁴ | Q |
|---|---|---|---|---|
| 4-hydroxyphenyl | " | " | " | " |
| 4-hydroxyphenyl | ethyl | " | " | (structure: H₃C—N attached to ring with —CH₂S, N, OH, O) |
| 1,4-cyclohexadienyl | " | " | " | " |
| phenyl | " | " | " | chloro |
| phenyl | acetyl | " | " | " |
| 4-hydroxyphenyl | ethyl | " | " | " |
| 3-hydroxyphenyl | " | acetoxy | acetoxy | " |
| 1,4-cyclohexadienyl | " | methyl | H | " |
| 2-amino-thiazol-4-yl | " | hydroxy | hydroxy | methoxymethyl |
| 1,4-cyclohexadienyl | " | " | " | " |
| 4-hydroxyphenyl | methyl | " | " | " |
| 4-hydroxyphenyl | " | " | " | carbamoyloxymethyl |
| 4-hydroxyphenyl | acetyl | acetoxy | acetoxy | " |
| 4-methoxyphenyl | ethyl | H | H | " |
| phenyl | " | " | " | N—methylcarbamoyl-oxymethyl |
| 2-thienyl | " | hydroxy | hydroxy | N—methylcarbamoyl-oxymethyl |
| 2-furyl | methyl | " | " | N—methylcarbamoyl-oxymethyl |
| phenyl | ethyl | " | " | pyridiniummethyl |
| phenyl | H | " | " | " |
| phenyl | " | H | H | " |
| 4-hydroxyphenyl | ethyl | Cl | H | " |
| phenyl | ethyl | hydroxy | hydroxy | 4-hydroxymethyl-pyridiniummethyl |
| 4-hydroxyphenyl | " | " | " | 4-hydroxymethyl-pyridiniummethyl |
| 4-hydroxyphenyl | " | " | " | 3-carbamoylpyridinium-methyl |
| 1,4-cyclohexadienyl | " | H | H | 3-carbamoylpyridinium-methyl |
| 2-thienyl | " | acetoxy | acetoxy | 3-acetylpyridinium-methyl |
| phenyl | " | hydroxy | hydroxy | (structure: —CH₂—S— triazole with CH₂—CH₂OH) |
| 4-hydroxyphenyl | " | " | " | " |
| 4-hydroxyphenyl | " | " | " | 4-carbamoyl-pyridiniummethyl |
| " | " | acetoxy | acetoxy | 4-carbamoyl-pyridiniummethyl |
| phenyl | " | " | " | 4-carbamoyl-pyridiniummethyl |
| " | " | hydroxy | hydroxy | (structure: —CH₂—S— tetrazole fused system with NH) |
| 4-hydroxyphenyl | " | " | " | " |

-continued

| R | R² | R³ | R⁴ | Q |
|---|---|---|---|---|
| " | " | " | " | (structure with —CH₂—S— triazole-thiadiazole) |
| phenyl |  | H | " | " |

A preferred group of compounds of this invention includes those formula 1 to 2 compounds wherein R is phenyl, 3-hydroxyphenyl, 4-hydroxyphenyl, 2-aminothiazol-4-yl, 2-thienyl or 1,4-cyclohexadienyl. More preferred are those compounds wherein R is phenyl or 4-hydroxyphenyl.

A further preferred group of compounds of this invention includes the formula 1 compounds wherein the dihydrocinnolin-4-one group is selected from the following:

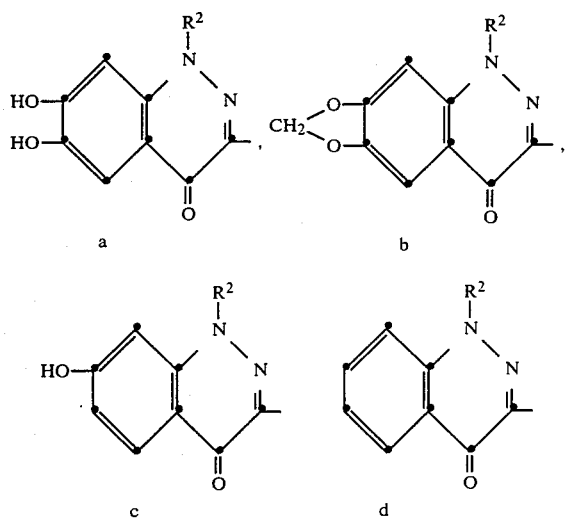

and the formula 2 compounds wherein the cinnoline moiety is selected from

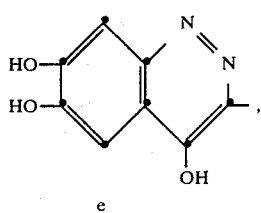

More preferred are those compounds of formula 1 wherein R² is a $C_1$–$C_3$-alkyl group. An additional preferred group are those compounds wherein R is a 4-hydroxyphenyl, a 2,3-dihydroxyhenyl, a 3,4-dihydroxyphenyl or a 3,4,5-trihydroxyphenyl group.

Still another preferred group of this invention are those compounds wherein the Q substituentsin formulas 1 and 2 are represented by the formula —CH₂Q¹ and Q¹ is as previously defined. Preferred groups represented by Q¹ are acetoxy, carbamoyloxy, methoxy, chloro, pyridinium or a group of the formula —SQ³ wherein Q³ is as defined supra. Of these, the —SQ³ group is especially preferred. More preferred Q³ groups are

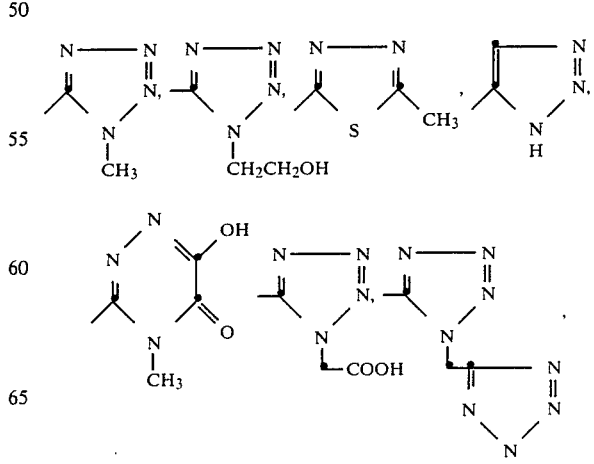

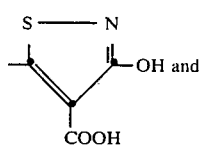 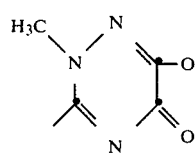 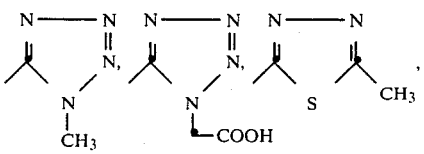

Accordingly, especially preferred compounds of this invention are represented by formula 11

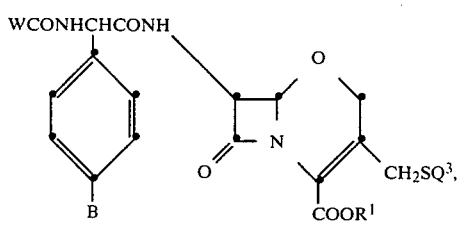

wherein
B is hydrogen or hydroxy;
W is a group selected from a–g:

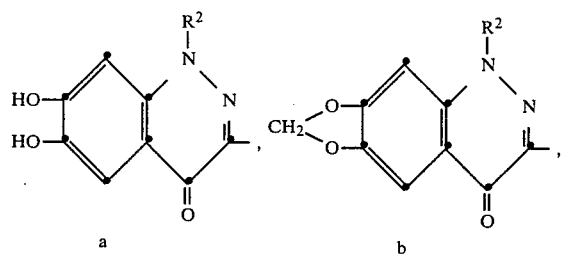

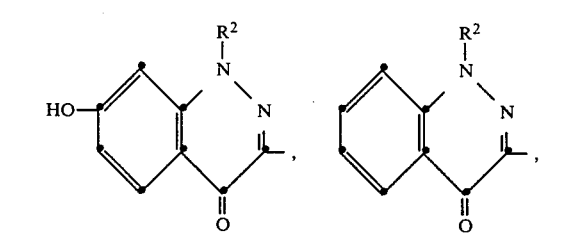

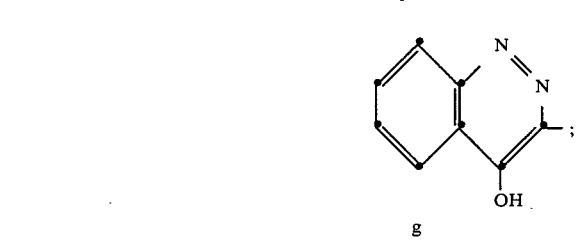

$Q^{3'}$ is a heteroaryl group selected from

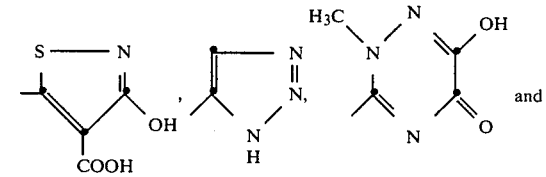

and their salts. Salts which are pharmaceutically acceptable are most preferred.

The compounds of the formulas 1 and 2 wherein $R^1$ is hydrogen or a biologically labile ester group and the pharmaceutically acceptable salts of those compounds wherein $R^1$ is hydrogen are broad spectrum antibiotics. These compounds are effective in inhibiting the growth of gram-negative microorganisms which are pathogenic to man and animals, for example, Pseudomonas andd Enterobactor. The compounds are also effective against gram-positive microorganisms such as Streptococcus and Staphylococcus.

The antibiotic compounds and the pharmaceutically acceptable salts thereof represented by formulas 1 and 2 wherein $R^1$ is other than a carboxy-protecting group can be formulated into antibiotic formulations suitable for administration in the treatment of infectious. diseases. One aspect of this invention, therefore, is an antibiotic formulation comprising a compound of formulas 1 or to 2 wherein $R^1$ is hydrogen or a biologically labile ester group or a pharamaceutically acceptable salt of a compound wherein $R^1$ is hydrogen together with a pharmaceutical carrier. The antibiotic, preferably as a pharmaceutically acceptable salt, can be formulated into formulations suitable for parenteral administration, i.e., via the i.v., i.m. or s.c. routes or by suppository.

For intravenous use the antibiotic can be formulated with one of the commonly used intravenous fluids and administered by infusion. Such fluids as, for example, physiological saline, Ringer's solution or 5% dextrose can be used.

For intramuscular preparations, a sterile formulation of a suitable salt form of the compound of the invention can be formulated as, for example, the sodium salt in a pharmaceutical diluent such as Water-for-Injection, physiological saline, 5% glucose or as a suspension in a suitable pharmaceutically acceptable oil base, e.g. an ester of a long chain fatty acid such as ethyl oleate.

Alternatively the unit dosage form of the antibiotic can be a solution of the antibiotic or preferably a salt thereof in a suitable diluet in sterile, hermetically sealed ampoules. The concentration of the antibiotic in the unit dosage may vary, e.g. from about 2 percent to about 20 percent depending on the particular antibiotic, the solubility thereof and the dose desired by the physician.

In a further aspect of this invention there is provided a method for the treatment of infectious diseases in mammals, especially those caused by gram-negative microorganisms which as Pseudomonas and Enterobacter. This method comprises administering to the mammal a dose between about 50 mg/kg and about 500 mg/kg of a formula 1 or 2 compound wherein $R^1$ is other than a carboxy-protecting group or a pharmaceutically acceptable salt thereof.

In practicing the above method the antibiotic can be administered in a single daily dose or in multiple doses per day. The treatment regime may require administration over extended periods of time, e.g., for several days or for from two to three weeks. The amount per administered dose or the total amount administered will depend on such factors as the nature and severity of the infection, the age and general health of the patient, the tolerance of the patient to the antibiotic and the microorganism or microorganisms involved in the infection.

A convenient method of practicing the treatment method is to administer the antibiotic via i.v. infusion. In this procedure the antibiotic is incorporated in a solution of a physiological fluid, such as 5% dextrose, and the solution infused slowly i.v. Alternatively the piggy back method of i.v. infusion can also be used.

A preferred method of this invention comprises administering the antibiotic of formula 11 wherein $R^1$ is other than a carboxy-protecting group or a salt thereof. An especially preferred method comprises administering 7-[[[[(1-ethyl-1,4-dihydro-6,7-dihydroxy-4-oxo-cinnolin-3-yl)carbonyl]amino](4-hydroxyphenyl)-acetyl]amino]-3-[[(1-methyl-1H-tetrazol-5-yl)thio]-methyl]-1-oxa-dethiaceph-3-em-4-carboxylic acid.

In the examples, the following abbreviations are used:

THF=tetrahydrofuran; DMF=N,N-dimethylformamide; BSA=bis-(trimethylsilyl)acetamide. When pH adjustments are made, 1N HCl or NaOH is used, depending on the adjustment being made. Products may be purified using chromatography, especially high performance liquid chromatography.

PREPARATION 1

Cinoxacin Acid Chloride

1-Ethyl-1,4-dihydro-4-oxo[1,3]dioxolo[4,5-g]-cinnolin-3-carboxylic acid (referred to herein as cinoxacin) (524 mg, 2 mmole) was stirred in oxalyl chloride (10 ml) at 45° C. After one hour the reaction mixture (a thick suspension) was removed from the heat; after cooling 1.5 hours, the mixture was evaporated to dryness under vacuum.

PREPARATION 2

Desethylcinoxacin Acid Chloride

Desethylcinoxacin (464 mg, 2 mmole) and oxalyl chloride (10 ml) were stirred together at 40° C.; after 10 minutes, dry DMF (2 drops) was added. The reaction mixture was stirred at 40° C. for 3 hours and then was evaporated to dryness under vacuum.

PREPARATION 3

Desethyl-de(methylenedioxy)cinoxacin Acid Chloride

Desethyl-de(methylenedioxy)cinoxacin (380 mg, 2 mmole) was stirred as a suspension in oxalyl chloride (7 ml), and DMF (2 drops) was added. After the suspension was stirred for 2 hours, it was evaporated under vacuum to dryness.

PREPARATION 4

7-(Dimethylamino)-1-ethyl-4-oxo-[1,3-dioxolo[4,5-g]-cinnolin]-3-carboxylic acid chloride Thionyl chloride (145 μl) and DMF (155 μl) were added to dichloromethane (3 ml) and stirred for 30 minutes. To this was added a solution of 1-ethyl-1,4-dihydro-6,7-dihydroxy-4-oxo-cinnolin-3-carboxylic acid chloride (250 mg) and triethylamine (555 μl) in dichloromethane (2.5 ml). The reaction mixture was stirred for an hour and then evaporated under vacuum.

EXAMPLE 1

7-[[[[(1-Ethyl-1,4dihydro-4-oxo[1,3]dioxolo[4,5-g]-cinnolin-3-yl)carbonyl]amino](4-hydroxyphenyl) acetyl]-amino]-3-[[(1-methyl-1H-tetrazol-5-yl)thio]-methyl-1-oxa-dethiaceph-3-em-4-carboxylic Acid

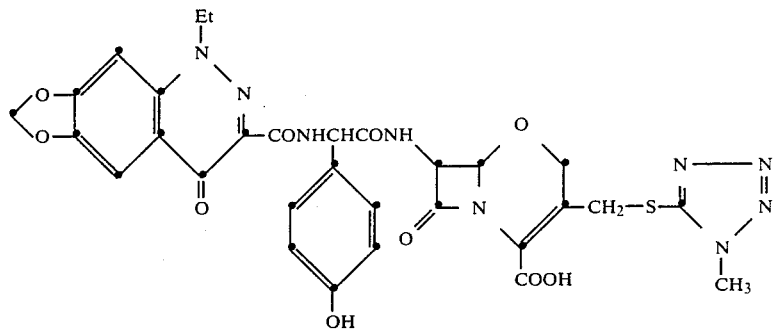

7-[[Amino(p-hydroxyphenyl)acetyl]amino[-3-[[(1-methyl-1H-tetrazol-5-yl) thio]methyl]-1-oxa-dethiaceph-3-em-4-carboxylic acid (2 mmole) is stirred in dry acetonitrile (10 ml). The mixture is cooled in an acetone-ice bath while BSA (8.8 mmole) is added. When the cephem is completely dissolved, a solution of cinoxacin acid chloride in dry acetonitrile (25 ml) is added dropwise. After the addition is complete, the solution is permitted to stand until the reaction is complete. The reaction mixture is purified by precipitation and extraction techniques to give the title compound.

EXAMPLE 2

7-[[[[(4-Hydroxy[1,3]dioxolo[4,5-g]cinnolin-3yl)-carbonyl]amino](4-hydroxyphenyl)acetyl]amino]-3-[[(1-methyl-1H-tetrazol-5-yl)thio]methylll]-1-oxa-dethiaceph-3em-4-carboxylic acid

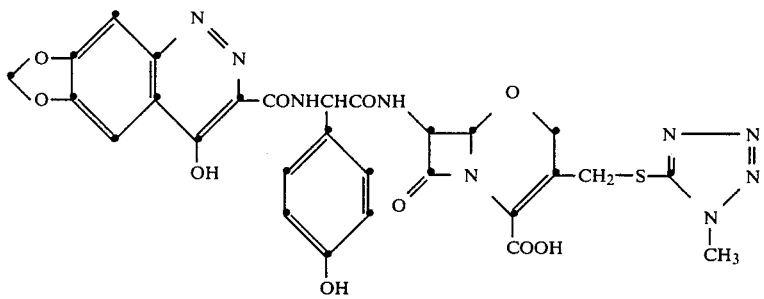

The NO-bis(trimethylsilyl) derivative of 7-[[amino-(4-hydroxyphenyl)acetyl]amino]-3-[[(1-methyl-1H-tetrazol-5-yl)thio]methyl]-1-oxa-dethyiaceph-3-em-4-carboxylic acid, in an acetonitrite solution, is prepared as described in Example 1. This solution is reacted with desethylcinoxacin acid chloride in dry acetonitrile (70 ml) until the reaction is complete. The reaction mixture is separated by precipitation and extraction techniques to give the title compound.

EXAMPLE 3

7-[[[[(4-Hydroxycinnolin-3-yl)carbonyl]amino](4-hydroxphenyl) acetyl]amino]-3-[[(1-methyl-1H-tetrazol-5-yl)thio]methyl]-1-oxa-dethiaceph-3-em-4-carboxylic Acid

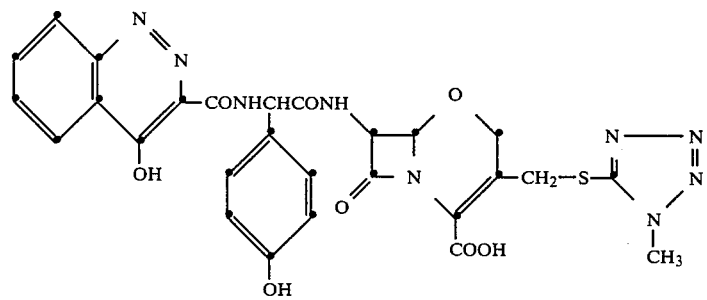

7 [[Amino(4-hydroxyphenyl)acetyl]amino]-3-[[1-methyl-1H-tetrazol-5-yl)thio]methyl]-1-dethiaceph-3-em-4-carboxylic acid trifluoroacetate salt (2.5 mmole) is stirred in dry acetonitrile (12.5 ml ) in an ice bath. BSA (8.75 mmole) is added. The resulting solution is stirred in ice/acetone bath while a suspension of cinoxacin acid chloride in acetonitrile (50 ml) is slowly added. After the reaction is complete, the reaction mixture is separated by precipitation and extraction techniques to give the title compound.

EXAMPLE 4

7-[[[[(1-Ethyl-1,4dihydro-4oxo[1,3]dioxolo[4,5-g]-cinnolin-3-yl)carbonyl] amino](4-hydroxyphenyl)acetyl]-amino]-3-[[(1-methyl-1H-tetrazol-5-yl)thio]methyl]-1-oxa-dethiaceph-3-em-4-carboxylic Acid

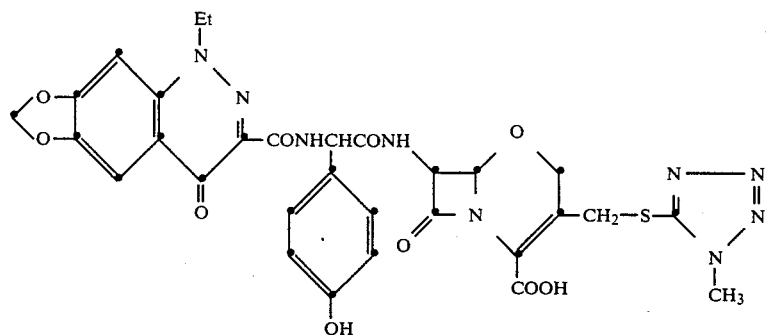

1-Ethyl-1,4-dihydro-3-[(imidazol-1-yl)carbonyl]-4-oxo[1,3]dioxolo[4,5-g]cinnoline (1 mmole) is stirred in dry DMF (4.5 ml) in an ice/acetone bath. To this is slowly added a stirred suspension of 7-[[amino-(phenyl) acetyl]amino]-3-[[(1-methyl-1H-tetrazol-5-yl)-thio]methyl]-1-oxa-dethiacepha-3-em-4-carboxylic acid (1.1 mmole) in acetonitrile (8 ml) to which triethylamine (1.05 mmole) is added. The mixture is removed from the cold bath and stirred at room temperature until the reaction is complete. The reaction mixture is separated by precipitation and extraction techniques to give the title compound.

EXAMPLE 5

7[[[[(4-Hydroxy[1,3]dioxolo[4,5-g]cinnolin-3-yl)-carbonyl]amino](4-hydroxphenyl)acetyl]amino]-3-[[(4,5-dihydro-6-hydroxy-4-methyl-5-oxo-1,2,4-triazin-3-yl)thio methyl]-1-oxa-dethiaceph-3-em-4-carboxylic Acid

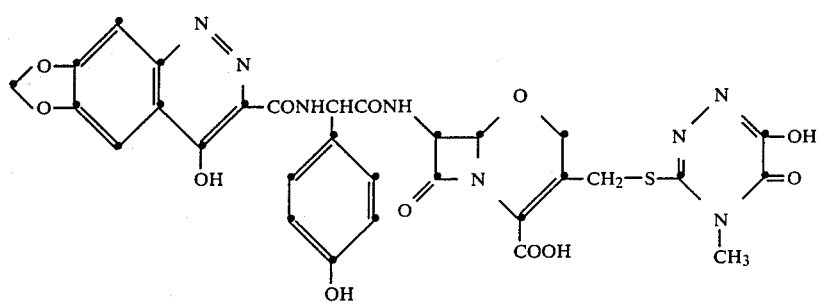

Desethycinoxacin (2 mmole) and oxalyl chloride (10 ml) are stirred in an oil bath at 40° C. DMF (2 drops) is added. After 2.5 hours, the mixture is removed from the heat and evaporated under vacuum to dryness.

7-[[Amino(4-hydroxyphenyl)acetyl]amino]-3-[[(4,5-dihydro-6-hydroxy-4-methyl-5-oxo-1,2,4-triazin-3-yl)thio]methyl]-1-oxa-dethiaceph-3-em-4-carboxylic acid as the trifluoroacetate salt (2.3 mmole) is stirred in dry acetonitrile (11.5 ml) in an ice bath, and BSA (9.2 mmole) is added. The solution is stirred in an acetone-/ice bath while a suspension of the desethylcinoxacin acid chloride in dry acetonitrile (50 ml) is slowly added. After the reaction is complete, the reaction mixture is separated, using precipitation and extraction techniques, to give the title compound.

EXAMPLE 6

7-[[[[(4-Hydroxycinnolin-3-yl)carbonyl]amino](4-hydroxyphenyl)acetyl]amino]-3-[[(4,5-dihydro-6-hydroxy-4-methyl-5-oxo-1,2,4-triazin-3-yl)thio]methyl]-1-oxadethiaceph-3-em-4-carboxylic Acid

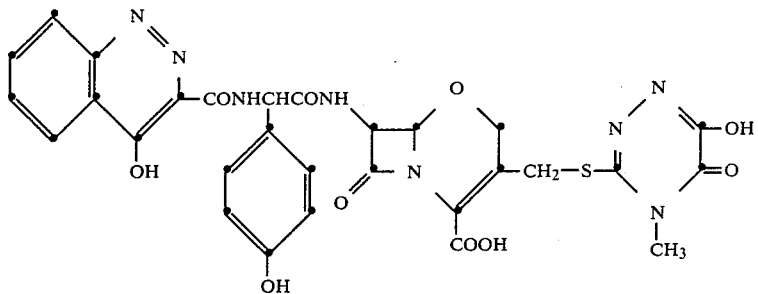

7-[[Amino(4-hydroxyphenyl)acetyl]amino]-3-[[(4,5-dihydro-6-hydroxy-4-methyl-5-oxo-1,2,4-triazine-3-yl)thio]methyl]-1-oxa-dethiaceph-3-em-4-carboxylic acid trifluoroacetate salt (2.3 mmole) is silylated as described in Example 5. The solution of silylated compound is stirred in an acetone/ice bath while a suspension of the desethyl-de(methylenedioxy)cinoxacin acid chloride in acetone (50 ml) is slowly added. The reaction is continued until complete, and then the reaction mixture is separated by precipitation and extraction techniques to give the title compound.

EXAMPLE 7

7-[[[[(1-Ethyl-1,4-dihydro-6,7-dihydroxy-4-oxo-cinnolin-3-yl)carbonyl]amino](4-hydroxyphenyl)acetyl]amino]-3-[[(1-methyl-1H-tetrazol-5-yl)thio]methyl]-1-oxa-dethiaceph-3-em-4-carboxylic Acid

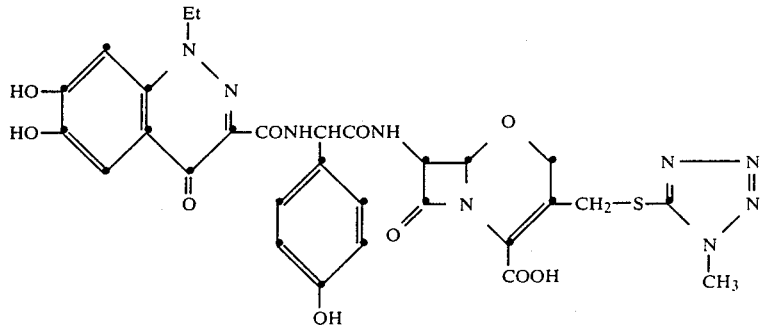

7-(Dimethylamino)-b 1-ethyl-4-oxo-[1,3]dioxolo-[4,5-g]cinnolin-3-carboxylic acid chloride, prepared from the corresponding acid as described in Preparation 4, is dissolved in acetonitrile and added to a solution of 7-[[amino(p-hydroxyphenyl)acetyl]amino]-3-[[(1-methyl-1H-tetrazol-5-yl)thio]methyl]-1-oxa-dethiaceph-3-em-4-carboxylic acid as the trifluoroacetate salt and BSA in acetonitrile. The resulting mixture is stirred until the reaction is complete and then is separated by precipitation and extraction procedures to give the title compound.

EXAMPLE 8

7-[L-[[[(1-Ethyl-1,4-dihydro-6,7-dihydroxy-4-oxo-cinnolin-3-yl)carbonyl]amino]phenylacetyl]amino]-3-chloro-1-oxa-dethiaceph-3-em-4-carboxylic Acid

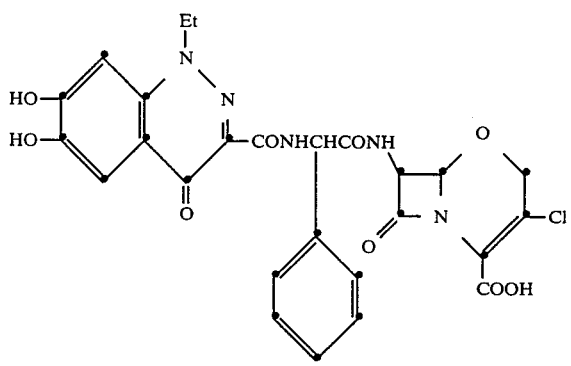

7-(Dimethylamino)-1-ethyl-4-oxo-[1,3]dioxolo-[4,5-g]cinnolin-3-carboxylic acid chloride, prepared from 750 mg (3 mmole) of the corresponding acid as described in Preparation 4, is dissolved in acetonitrile (10 ml) and added to a solution of cefachlor monohydrate (3 mmole) and monosilyltrifluoroacetamide (24 mmole) in acetonitrile (10 ml). The resulting mixture is stirred until the reaction is complete and then is separated, using precipitation and extraction techniques, to give the title compound.

EXAMPLE 9

7-[[[[(1-Ethyl-1,4-dihydro-6,7-dihydroxy-4-oxo-cinnolin-3-yl)carbonyl]amino](4-hydroxyphenyl)acetyl]amino]-3-[[(1-carboxymethyl)-1H-tetrazol-5-yl)thio]methyl]-1-oxa-dethiaceph-3-em-4-carboxylic Acid

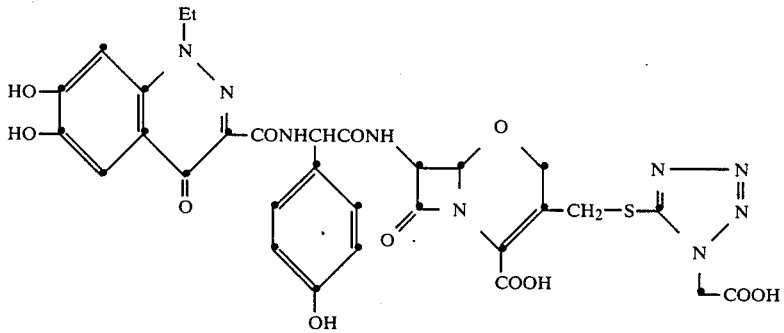

7-(Dimethylamino)-1-ethyl-4-oxo-[1,3]dioxolo-[4,5-g]cinnolin-3-carboxylic acid chloride, prepared from 477 mg (1.9 mmole) of the corresponding acid as described in Preparation 4, is dissolved in acetonitrile (11 ml). This suspension is added slowly to a solution of 7-[[amino(4-hydroxyphenyl)acetyl]amino]-3-[[[(1-carboxymethyl)-1H-tetrazol-5-yl]thio]methyl]-1-oxa-dethiaceph-3-em-4-carboxylic acid trifluoroacetate salt (1.26 mmole) in THF (5.5 ml) and water (7.3 ml) which has been adjusted to pH 8.0. The addition is carried out in an ice/water bath, and the pH is kept at 8.0 with 0.5N NaOH. After the addition is complete, the reaction mixture is stirred until the reaction is complete and then is separated, using precipitation and extraction techniques, to give the title compound.

EXAMPLE 10

7-[[[[(1-Ethyl-1,4-dihydro-6,7-dihydroxy-4-oxo-cinnolin-3-yl)carbonyl]amino](4-hydroxyphenyl)acetyl]amino]-1-oxa-dethiacephalosporanic Acid

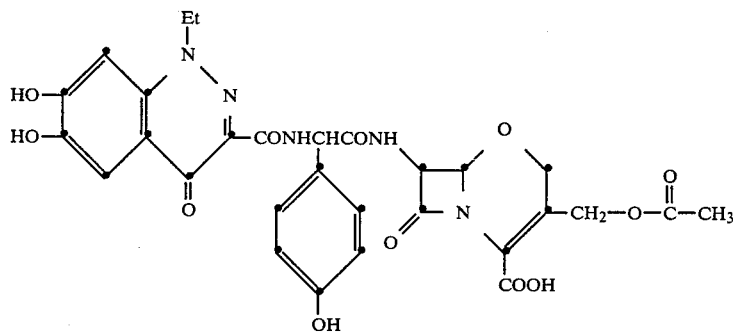

7-(Dimethylamino)-1-ethyl-4-oxo-[1,3]dioxolo-[4,5-g]cinnolin-3-carboxylic acid chloride, prepared from 1.12 g (4.5 mmole) of the corresponding acid as described in Preparation 4, is reacted with 7-[[amino-(4-hydroxyphenyl)acetyl]amino]-1-oxa-dethiacephalosporanic acid (3 mmole), using a procedure like that of Example 9. The reaction mixture is separated, using precipitation and extraction techniques, to give the title compound.

EXAMPLE 11

7-[L-[[[(1-Ethyl-1,4-dihydro-6,7-dihydroxy-4-oxo-cinnolin-3-yl)amino]phenylacetyl]amino]-3-[[(1-methyl-1H-tetrazol-5-yl)thio]methyl]-1-oxa-dethiaceph-3-em-4-carboxylic Acid

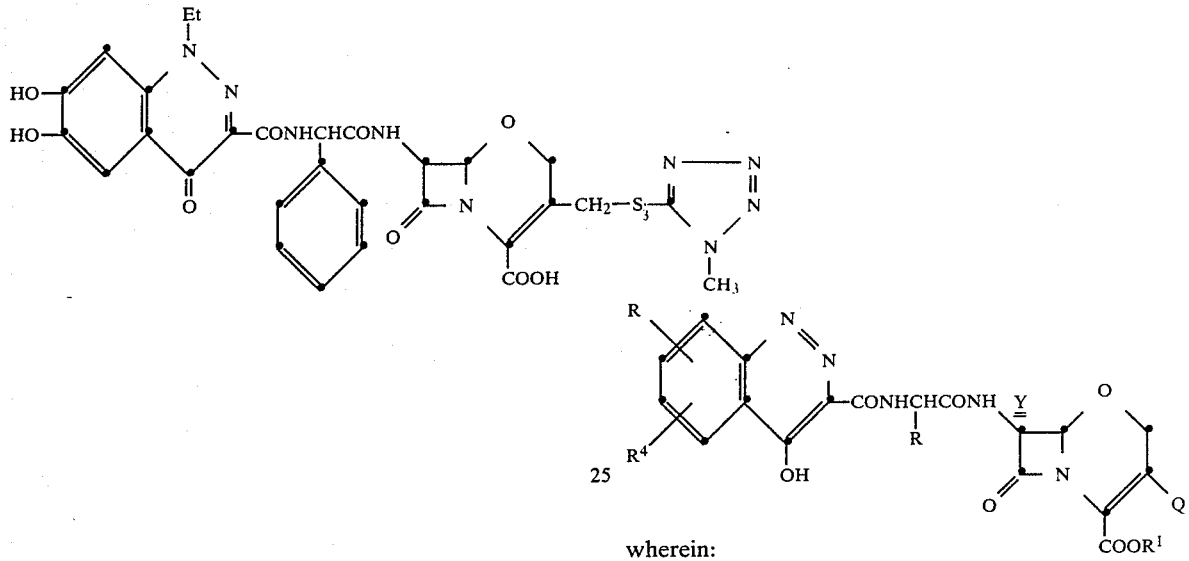

7-(Dimethylamino)-1-ethyl-4-oxo-[1,3]dioxolo-[4,5-g]cinnolin-3-carboxylic acid chloride, prepared from 550 mg (2.2 mmole) of the corresponding acid as described in Preparation 4, is dissolved in acetonitrile (12.5 ml). This is added slowly to a solution of 7-[L-[[amino(phenylacetyl)]amino]-3-[[[(1-carboxy-methyl)-1H-tetrazol-5-yl]thio]methyl]-1-oxa-dethiaceph-3-em-4-carboxylic acid trifluoroacetate salt (2 mmole) in THF (6.5 ml) and water (10 ml) which has been adjusted to pH 8.0 with 1N NaOH; the pH is kept at 8.0 with 0.5N NaOH. After completion the reaction mixture is separated, using precipitation and extraction techniques, to give the title compound.

EXAMPLE 12

7-[D-[[[(1-Ethyl-1,4-dihydro-6,7-dihydroxy-4-oxo-cinnolin-3-yl)amino]phenylacetyl]amino]-3-[[(1-methyl-1H-tetrazol-5-yl)thio]methyl]-1-oxa-dethiaceph-3-em-4-carboxylic Acid This compound is prepared using the procedure of Example 11 except that 7-[D-[[amino(phenyl)acetyl]amino]-3-[[[1-methyl-1H-tetrazol-5-yl]thio]methyl]-1-oxa-dethiaceph-3-em-4-carboxylic acid trifluoroacetate salt is used.

I claim:

1. A compound of formula 1 or 2:

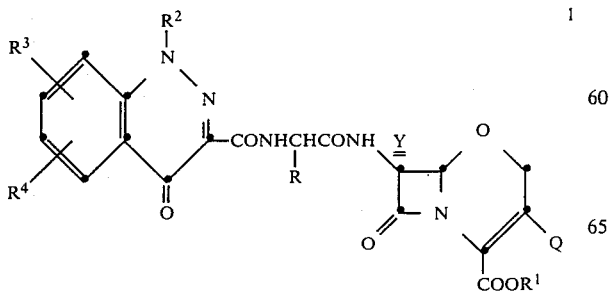

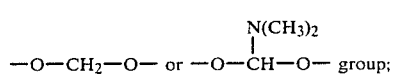

wherein:
R is phenyl which is optionally substituted by one or two hydroxy or $C_1$–$C_3$-alkoxy groups; cyclohexadienyl; cyclohexenyl; or 2-thienyl, 3-thienyl, 2-furyl, 3-furyl or 2-aminothiazol-4-yl, each of which is optionally substituted by one or two $C_1$–$C_3$-alkyl groups;

$R^1$ is hydrogen, a carboxy-protecting group or a biologically labile ester group;

$R^2$ is hydrogen, $C_1$–$C_3$-alkyl, acetyl, or $C_1$–$C_3$-alkylsulfonyl;

$R^3$ is hydroxy, $C_1$–$C_3$-alkoxy, $C_1$–$C_3$-alkyl, halo, $C_2$–$C_4$-alkanoyloxy, $C_1$–$C_3$-alkylsulfonyl, or $C_1$–$C_4$-alkylaminocarbonyloxy; and $R^4$ is hydrogen or $R^3$; or $R^3$ and $R^4$, when taken together on adjacent carbon atoms, form an $$-O-CH_2-O- \text{ or } -O-\underset{\underset{N(CH_3)_2}{|}}{CH}-O- \text{ group};$$

Y is hydrogen or methoxy;
Q is halo, methoxy, methyl or a group of the formula $-CH_2Q^1$ wherein $Q^1$ is
(a) $C_2$–$C_4$-alkanoyloxy;
(b) carbamoyloxy or $C_1$–$C_4$-alkylcarbamoyloxy;
(c) $C_1$–$C_4$-alkoxy;
(d) chloro, bromo or iodo;
(e) a heteroaryl group selected from

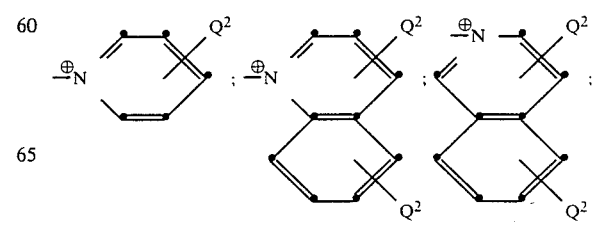

-continued

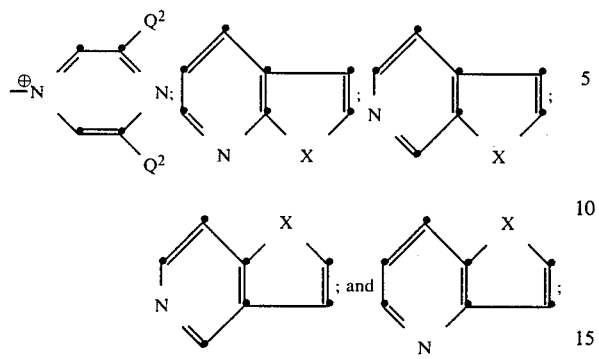

wherein
X is O, S, or —NH—;
$Q^2$ is hydrogen, $C_1$-$C_4$-alkyl,

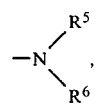

halo, hydroxy, hydroxymethyl, trifluoromethyl, carbamoyl, $C_1$-$C_4$-alkylcarbamoyl, carboxy, cyano, $C_1$-$C_3$-alkanoyl,

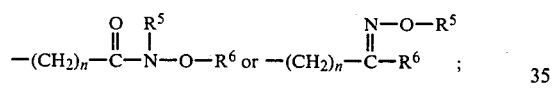

and
$R^5$ and $R^6$, independently, are hydrogen or $C_1$-$C_4$-alkyl;
(f) a group of the formula -$SQ^3$
  wherein $Q^3$ is
  (a') $C_1$-$C_4$-alkyl, phenyl or phenyl substituted with 1 or 2 groups selected from the group consisting of $C_1$-$C_4$-alkyl, $C_1$-$C_4$-alkoxy, halo, hydroxy, nitro, cyano, methanesulfonamido and trifluoromethyl;
  (b') a tetrazolyl group selected from

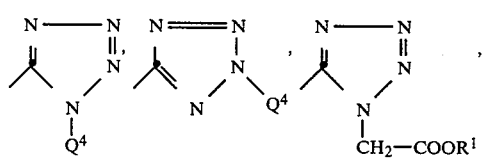

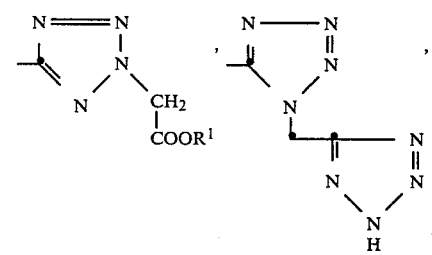

-continued

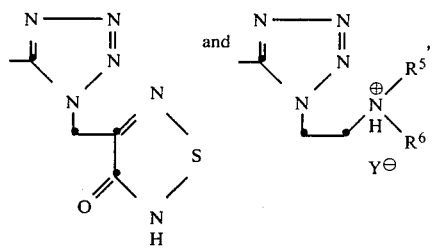

wherein Y is halo,
(c') a thiadiazolyl group selected from

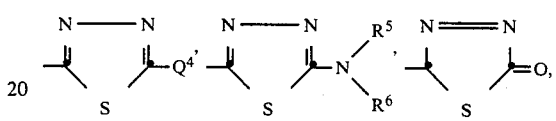

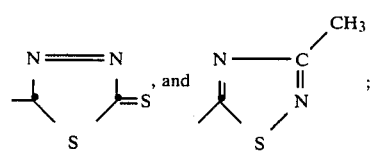

(d') an oxadiazolyl group of the formula

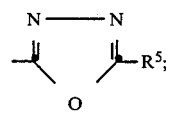

(e') a triazolyl group selected from

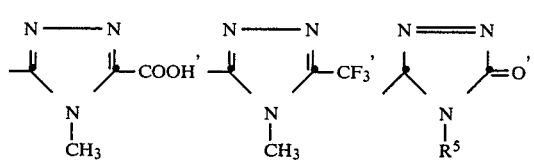

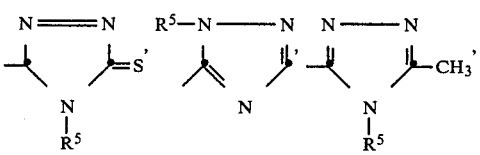

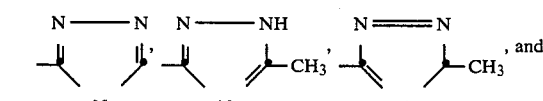

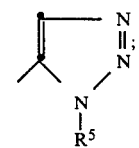

(f') a thiazolyl group selected from

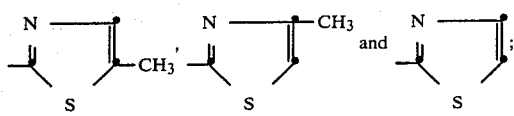

(g') an isothiazolyl group of the formula

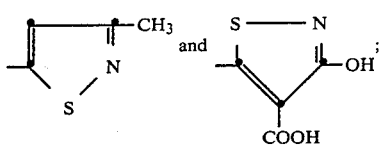

(h') an oxazolyl group of the formula

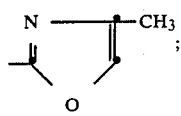

(i') a triazinyl group selected from

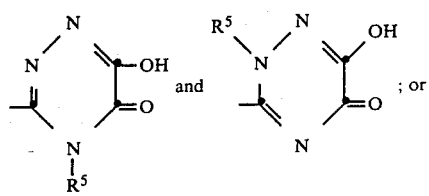

(j') a heteroaryl group selected from

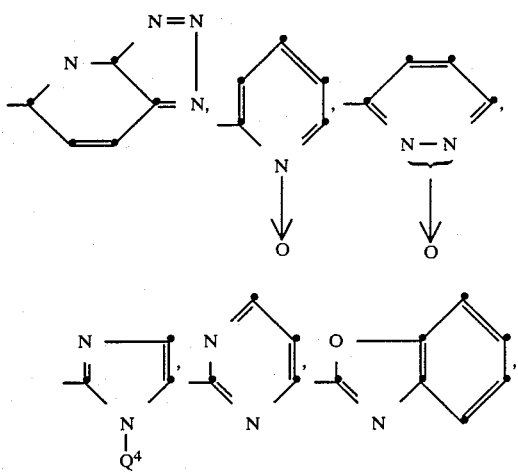

wherein $Q^4$ is hydrogen, $C_1$–$C_4$-alkyl, amino-$C_2$–$C_4$-alkyl, protected amino-$C_2$–$C_4$-alkyl or hydroxy-$C_2$–$C_4$-alkyl; or a salt of the formula 1 and 2 acids.

2. A compound of claim 1 which has formula 1.

3. A compound of claim 1 which has formula 2.

4. A compound of claim 1 wherein R is phenyl, 3-hydroxyphenyl, 4-hydroxyphenyl, 2-aminothiazol-4-yl, 2-thienyl or 1,4-cyclohexadienyl.

5. A compound of claim 4 wherein R is phenyl or 4-hydroxyphenyl.

6. A compound of claim 4 wherein $R^2$ is $C_1$–$C_3$-alkyl.

7. A compound of claim 1 wherein $R^3$ is hydroxy and $R^4$ is hydrogen.

8. A compound of claim 7 wherein $R^3$ and $R^4$ are hydroxy.

9. A compound of claim 1 wherein $R^3$ and $R^4$ are taken together on adjacent carbon atoms to form an —O—$CH_2$—O— group.

10. A compound of claim 7 which has formula 1.

11. A compound of claim 7 which has formula 2.

12. A compound of claim 1 wherein Y is hydrogen.

13. A compound of claim 1 wherein Y is methoxy.

14. A compound of claim 1 wherein Q is a —$CH_2Q^1$ substituent.

15. A compound of claim 14 wherein $Q^1$ is acetoxy, carbamoyloxy, methoxy, chloro, pyridinium or a group of the formula —$SQ^3$.

16. A compound of claim 15 wherein $Q^3$ is selected from

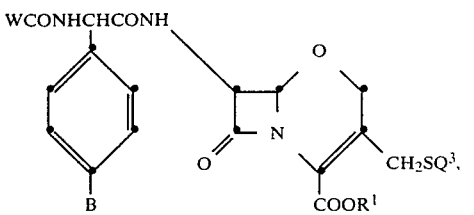

17. A compound of the formula

WCONHCHCONH wherein
B is hydrogen or hydroxy;
W is a group selected from:

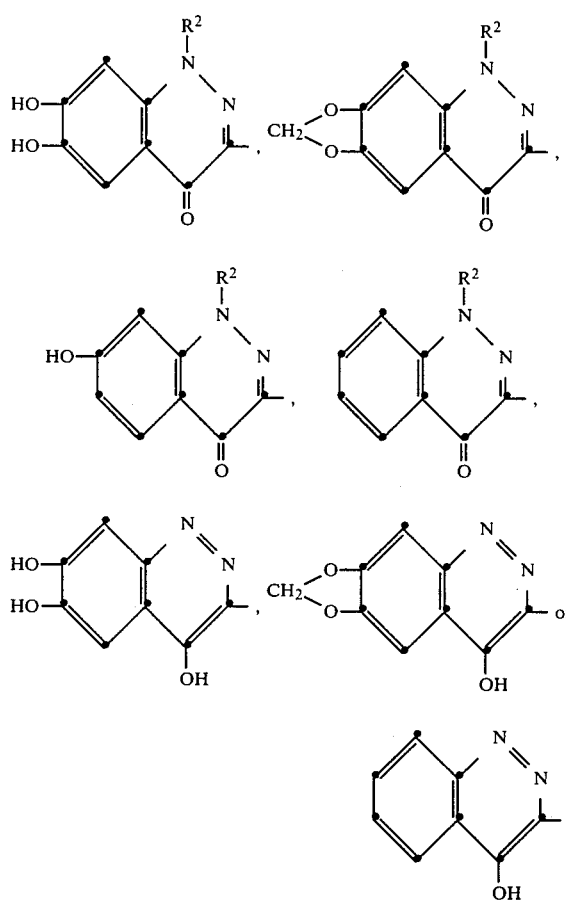

Q³' is a heteroaryl group selected from

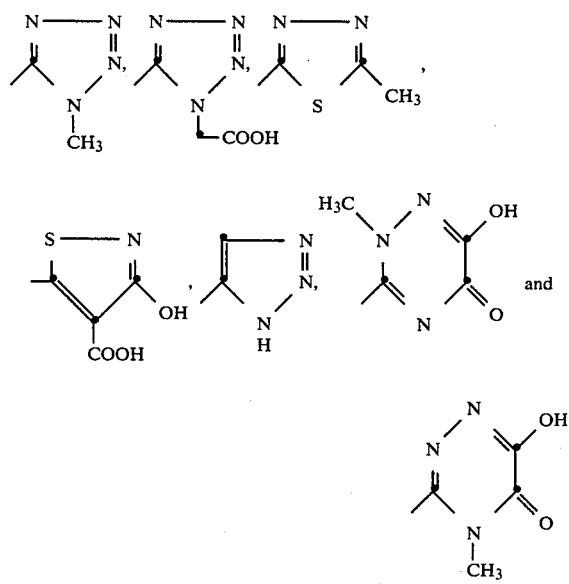

R¹ is hydrogen, a carboxy-protecting group or a biologically labile ester group; and R² is hydrogen, $C_1$-$C_3$-alkyl, acetyl or $C_1$-$C_3$-alkylsulfonyl; or a salt of the compounds wherein R¹ is hydrogen.

18. A compound of claim 1 wherein the salt is pharmaceutically acceptable.

19. A compound of claim 17 wherein the salt is pharmaceutically acceptable.

20. The compound of claim 1 which is 7-[[[[(4-hydroxycinnolin-3-yl)carbonyl]amino](4-hydroxyphenyl)acetyl]amino]-3-[[(1-methyl-1H-tetrazol-5-yl)thio]methyl]-1-oxa-dethiaceph-3-em-4-carboxylic acid.

21. The compound of claim 1 which is 7-[[[[(4-hydroxycinnolin-3-yl)carbonyl]amino](4-hydroxyphenyl)acetyl]amino]-3-[[(4,5-dihydro-6-hydroxy-4-methyl-5-oxo-1,2,4-triazin-3-yl)thio]methyl]-1-oxa-dethiaceph-3-em-4-carboxylic acid.

22. The compound of claim 1 which is 7-[[[[(1-ethyl-1,4-dihydro-6,7-dihydroxy-4-oxo-cinnolin-3-yl)carbonyl]amino](4-hydroxyphenyl)acetyl]amino]-3-[[(1-methyl-1H-tetrazol-5-yl)thio]methyl]-1-oxa-dethiaceph-3-em-4-carboxylic acid.

23. A compound of claim 1 which is 7-[L-[[[(1-ethyl-1,4-dihydro-6,7-dihydroxy-4-oxo-cinnolin-3-yl)carbonyl]amino]phenylacetyl]amino]-3-chloro-1-oxa-dethiaceph-3-em-4-carboxylic acid.

24. The compound of claim 1 which is 7-[[[[(1-ethyl-1,4-dihydro-6,7-dihydroxy-4-oxo-cinnolin-3-yl)carbonyl]amino](4-hydroxyphenyl)acetyl]amino]-3-[[(1-carboxymethyl)-1H-tetrazol-5-yl)thio]methyl]-1-oxa-dethiaceph-3-em-4-carboxylic acid.

25. The compound of claim 1 which is 7-[L-[[[(1-ethyl-1,4-dihydro-6,7-dihydroxy-4-oxo-cinnolin-3-yl)amino]phenylacetyl]amino]-3-[[(1-methyl-1H-tetrazol-5-yl)thio]methyl]-1-oxa-dethiaceph-3-em-4-carboxylic acid.

26. The compound of claim 1 which is 7-[D-[[[(1-ethyl-1,4-dihydro-6,7-dihydroxy-4-oxo-cinnolin-3-yl)amino]phenylacetyl]amino]-3-[[(1-methyl-1H-tetrazol-5-yl)thio]methyl]-1-oxa-dethiaceph-3-em-4-carboxylic acid.

27. A pharmaceutical formulation comprising a compound of claim 1 wherein R¹ is hydrogen or a biologically labile ester group or a pharmaceutically acceptable salt of a compound wherein R¹ is hydrogen together with a pharmaceutically acceptable diluent.

28. The formulation of claim 27 comprising a compound wherein Q has the formula —SQ³.

29. The formulation of claim 28 comprising 7-[[[[(1-ethyl-1,4-dihydro-6,7-dihydroxy-4-oxo-cinnolin-3-yl)carbonyl]amino](4-hydroxyphenyl)acetyl]amino]-3-[[(1-methyl-1H-tetrazol-5-yl)thio]methyl]-1-oxadethiaceph-3-em-4-carboxylic acid.

30. A method for treating infections in a mammal which comprises administering to said mammal a dose between about 50 mg/kg and about 500 mg/kg of a compound of claim 1 wherein R¹ is other than a carboxy-protecting group.

31. The method of claim 30 wherein a compound wherein Q is an —SQ³ group is administered.

32. The method of claim 31 wherein 7-[[[[(1-ethyl-1,4-dihydro-6,7-dihydroxy-4-oxo-cinnolin-3-yl)-carbonyl]amino](4-hydroxyphenyl)acetyl]amino]-3-[[(1-methyl-1H-tetrazol-5-yl)thio]methyl]-1-oxa-dethiaceph-3-em-4-carboxylic acid is administered.

* * * * *

UNITED STATES PATENT AND TRADEMARK OFFICE
CERTIFICATE OF CORRECTION

PATENT NO. : 4,503,052  
DATED : March 5, 1985  
INVENTOR(S) : William H. W. Lunn Page 1 of 3

It is certified that error appears in the above—identified patent and that said Letters Patent is hereby corrected as shown below:

Column 36, lines 15-25, that portion of the structural formula reading

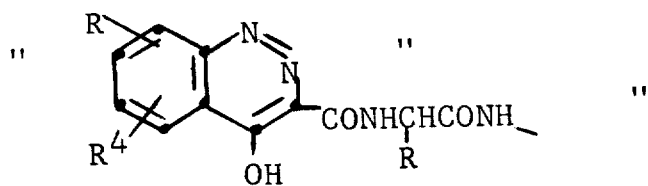

should read

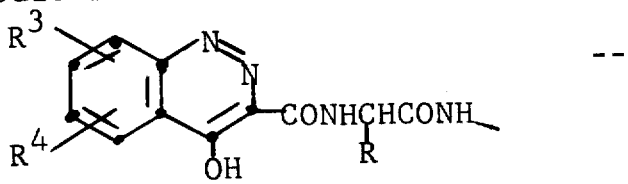

Column 39, lines 10-15,

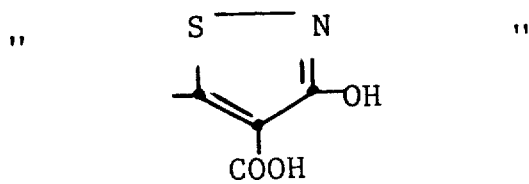

UNITED STATES PATENT AND TRADEMARK OFFICE
CERTIFICATE OF CORRECTION

PATENT NO. : 4,503,052  
DATED : March 5, 1985  
INVENTOR(S) : William H. W. Lunn Page 2 of 3

It is certified that error appears in the above—identified patent and that said Letters Patent is hereby corrected as shown below:

should read

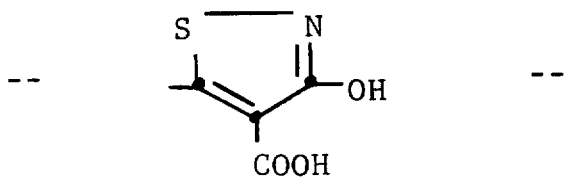

Column 40, lines 57-64, that portion of the structural formula reading

" 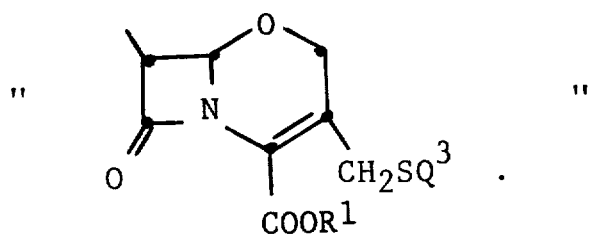 "  .

UNITED STATES PATENT AND TRADEMARK OFFICE
CERTIFICATE OF CORRECTION

PATENT NO. : 4,503,052

DATED : March 5, 1985

INVENTOR(S) : William H. W. Lunn

It is certified that error appears in the above—identified patent and that said Letters Patent is hereby corrected as shown below:

should read

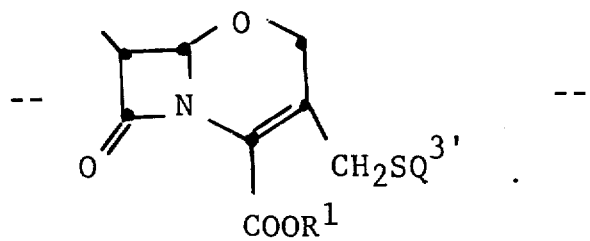

Signed and Sealed this

Sixth Day of May 1986

[SEAL]

Attest:

Attesting Officer

DONALD J. QUIGG

Commissioner of Patents and Trademarks

UNITED STATES PATENT AND TRADEMARK OFFICE
CERTIFICATE OF CORRECTION

PATENT NO. : 4,503,052

DATED : March 5, 1985

INVENTOR(S) : William H. W. Lunn

It is certified that error appears in the above-identified patent and that said Letters Patent is hereby corrected as shown below:

Column 40, line 10, "claim 7" should read -- claim 1 --.

Signed and Sealed this

Nineteenth Day of August 1986

[SEAL]

Attest:

Attesting Officer

DONALD J. QUIGG

Commissioner of Patents and Trademarks